US008529565B2

(12) United States Patent
Masuda et al.

(10) Patent No.: US 8,529,565 B2
(45) Date of Patent: Sep. 10, 2013

(54) ULTRASONIC OPERATING APPARATUS

(75) Inventors: Shinya Masuda, Hino (JP); Chie Yachi, Fuchu (JP); Kazunori Taniguchi, Hamburg (DE)

(73) Assignee: Olympus Medical Systems Corp. (JP)

( * ) Notice: Subject to any disclaimer, the term of this patent is extended or adjusted under 35 U.S.C. 154(b) by 1760 days.

(21) Appl. No.: 11/623,236

(22) Filed: Jan. 15, 2007

(65) Prior Publication Data
US 2008/0172051 A1 Jul. 17, 2008

(51) Int. Cl.
*A61B 18/18* (2006.01)
*A61B 17/32* (2006.01)

(52) U.S. Cl.
USPC .............................. 606/49; 606/170

(58) Field of Classification Search
USPC ......... 606/49, 169, 207, 159; 601/2; 604/22; 433/86, 119, 118; 600/437, 439, 459; 310/323.01, 323.19, 323.2, 325, 311
See application file for complete search history.

(56) References Cited

U.S. PATENT DOCUMENTS

| 6,193,709 | B1 * | 2/2001 | Miyawaki et al. ............... 606/1 |
| 6,251,110 | B1 * | 6/2001 | Wampler ........................ 606/49 |
| 6,340,352 | B1 | 1/2002 | Okada et al. |
| 6,623,500 | B1 * | 9/2003 | Cook et al. .................... 606/170 |
| 6,669,690 | B1 * | 12/2003 | Okada et al. .................... 606/40 |
| 2002/0057541 | A1 | 5/2002 | Donofrio |
| 2003/0130657 | A1 | 7/2003 | Tom et al. |
| 2003/0163131 | A1 * | 8/2003 | Manna et al. ................... 606/50 |
| 2005/0085803 | A1 | 4/2005 | Okabe |

FOREIGN PATENT DOCUMENTS

| EP | 1 040 792 | 4/2000 |
| JP | 2002-330977 | 11/2002 |
| JP | 2005-118357 | 5/2005 |

OTHER PUBLICATIONS

European Search Report relating to European Patent Application No. EP 08 00 0655.

* cited by examiner

*Primary Examiner* — Linda Dvorak
*Assistant Examiner* — Jaymi Della
(74) *Attorney, Agent, or Firm* — Ostrolenk Faber LLP

(57) ABSTRACT

An apparatus comprises an ultrasonic transducer, a probe portion, the proximal end being coupled to the ultrasonic transducer, ultrasonic waves output from the ultrasonic transducer being transmitted to the probe portion, a storage portion which stores the ultrasonic transducer, a cylindrical casing portion which has a distal end and a proximal end and which is installed outside the storage portion, an electric path provided to extend between an electric contact disposed at the distal end of the casing portion and an electric cable connecting portion provided at the proximal end of the casing portion, and an electric cable which has a distal end and a proximal end, the proximal end being connected to a power supply unit, the distal end being coupled to the electric cable connecting portion, the electric path being disposed between the storage portion and the casing.

6 Claims, 31 Drawing Sheets

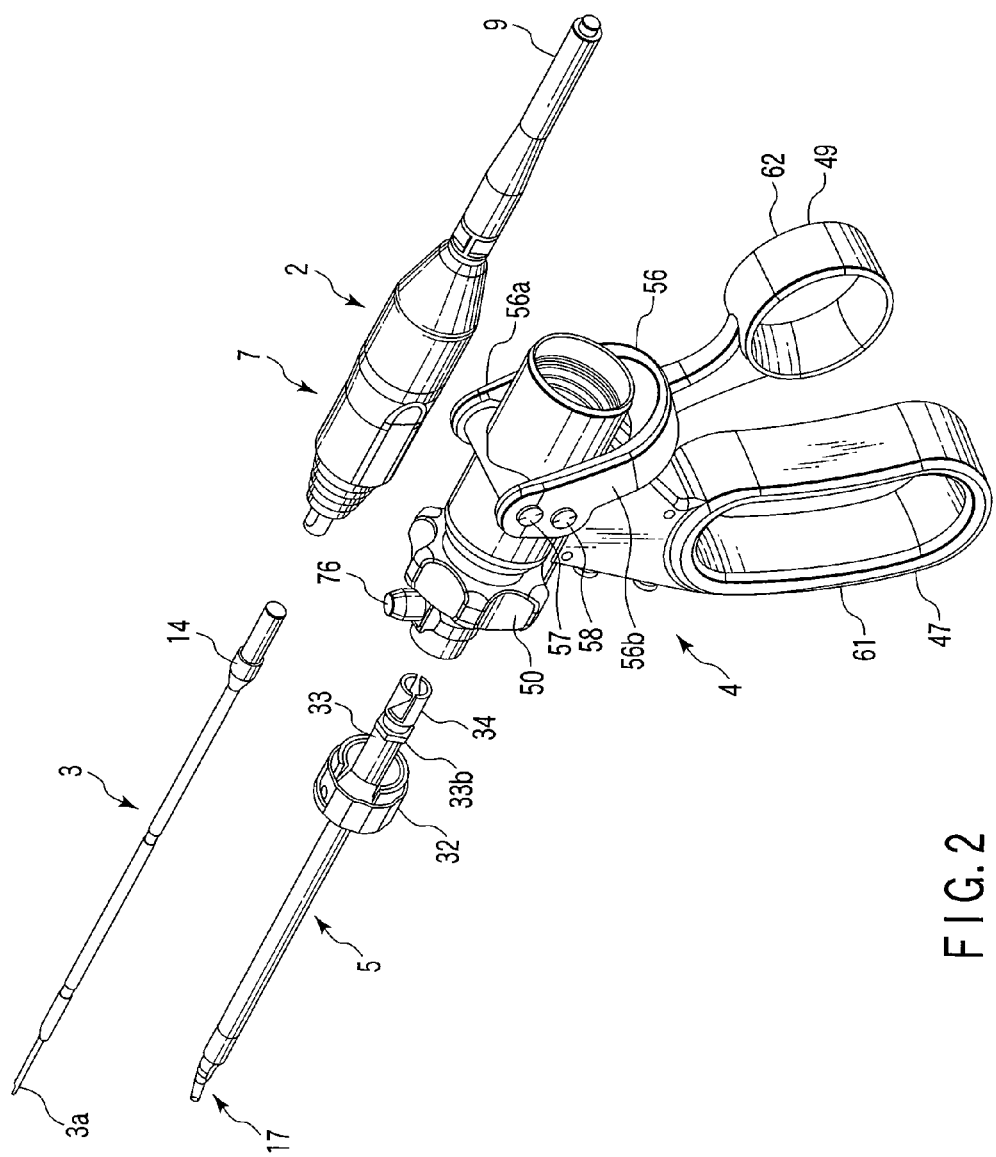
F I G. 2

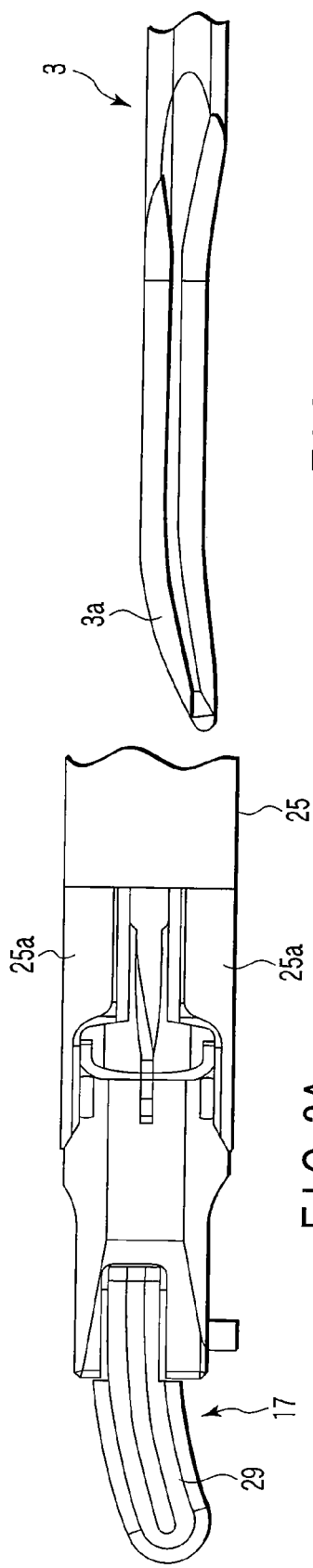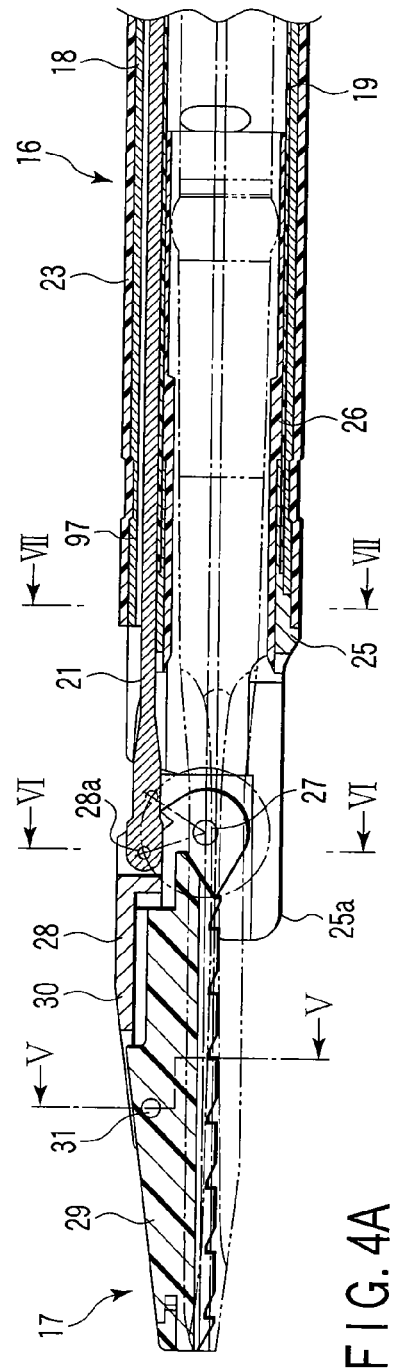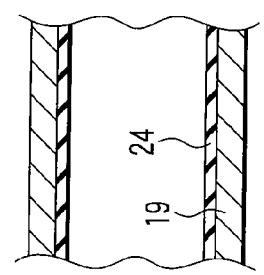

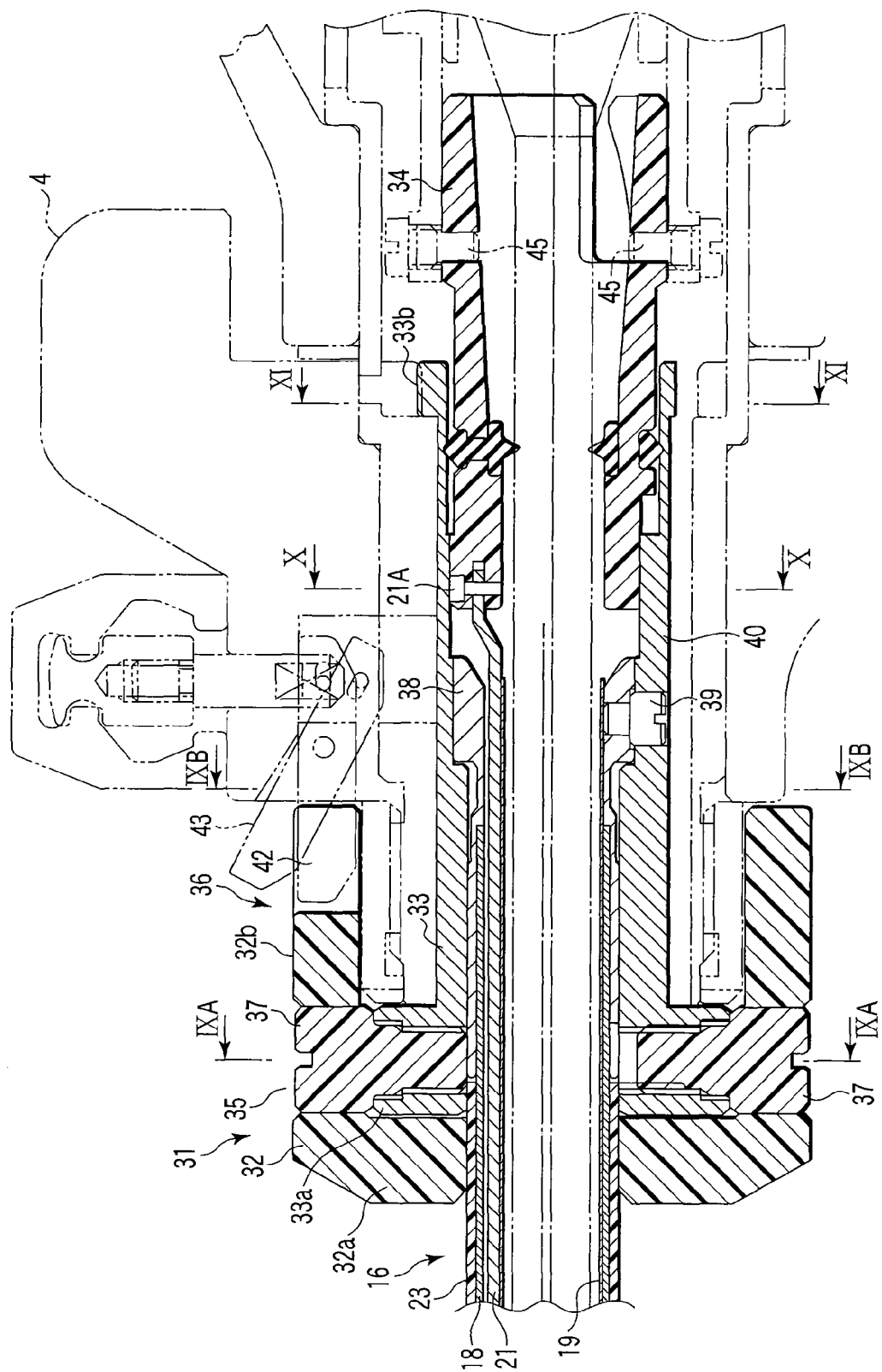
F I G. 8

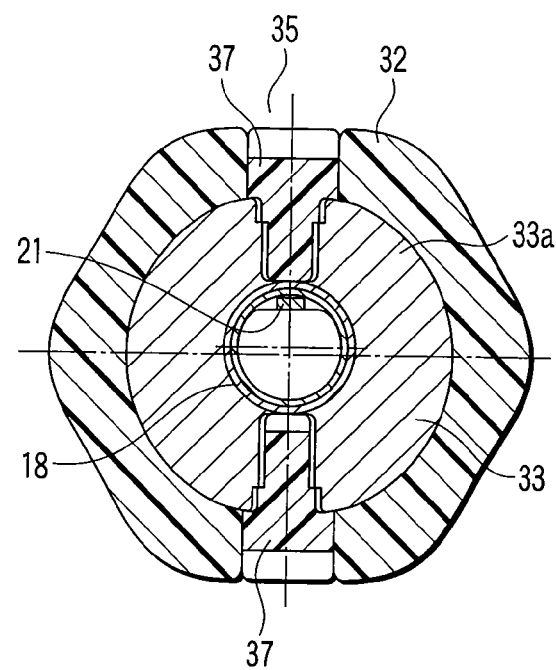
F I G. 9A
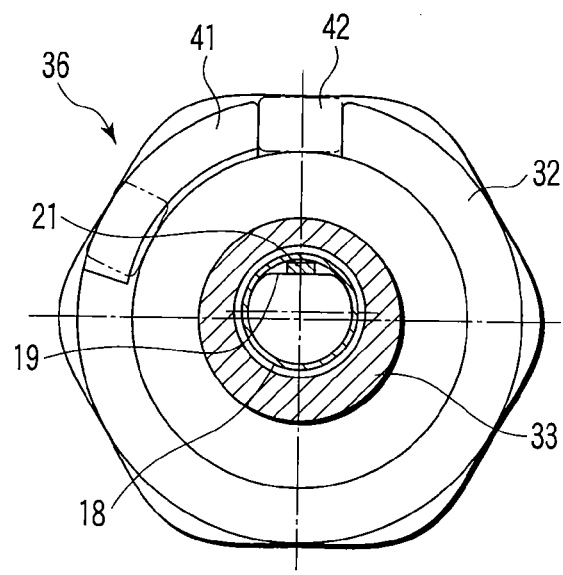
F I G. 9B

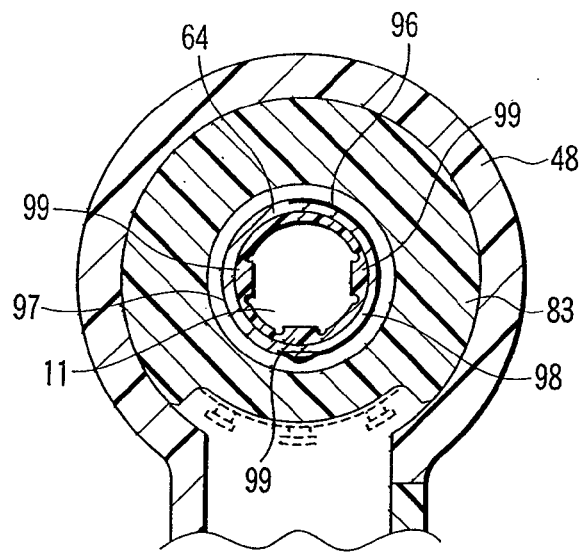
F I G. 21
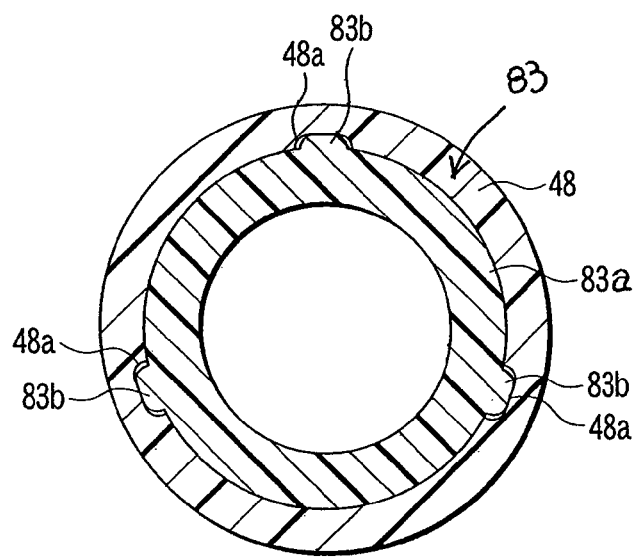
F I G. 22

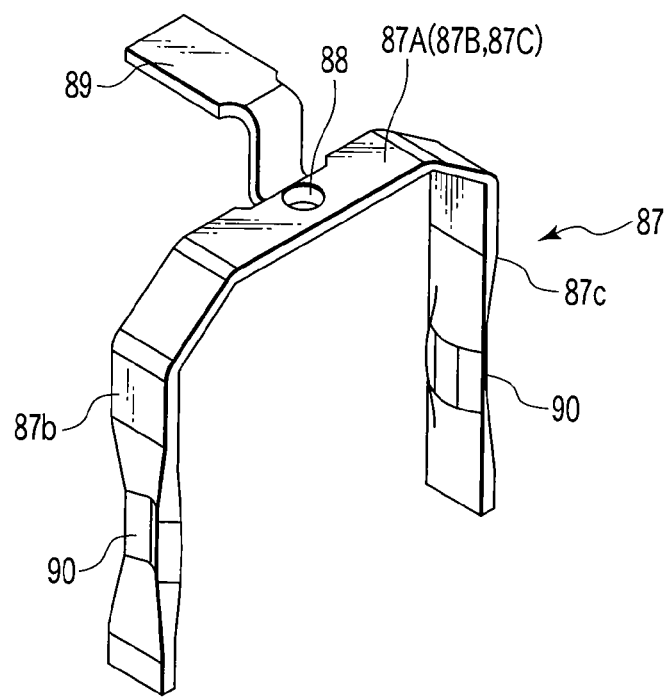
F I G. 29
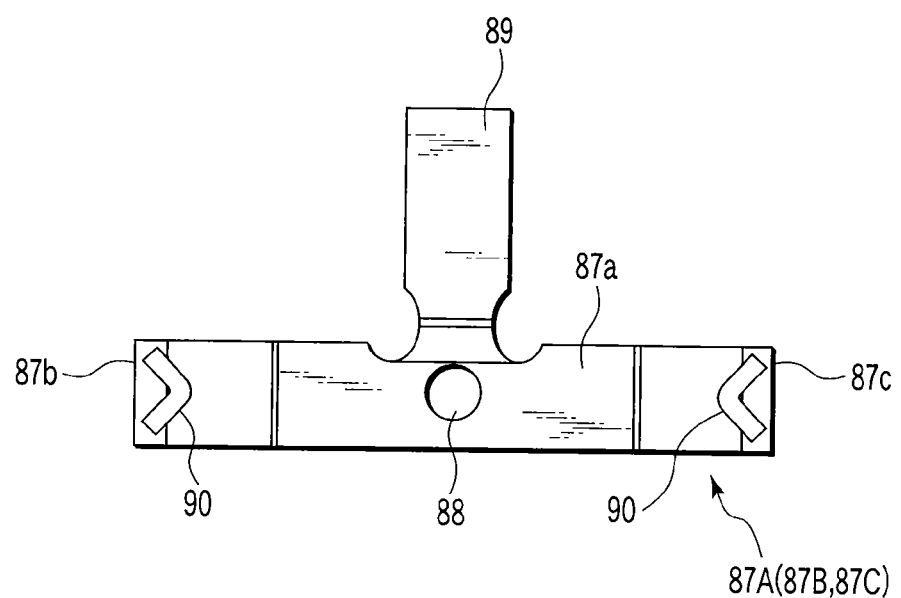
F I G. 30

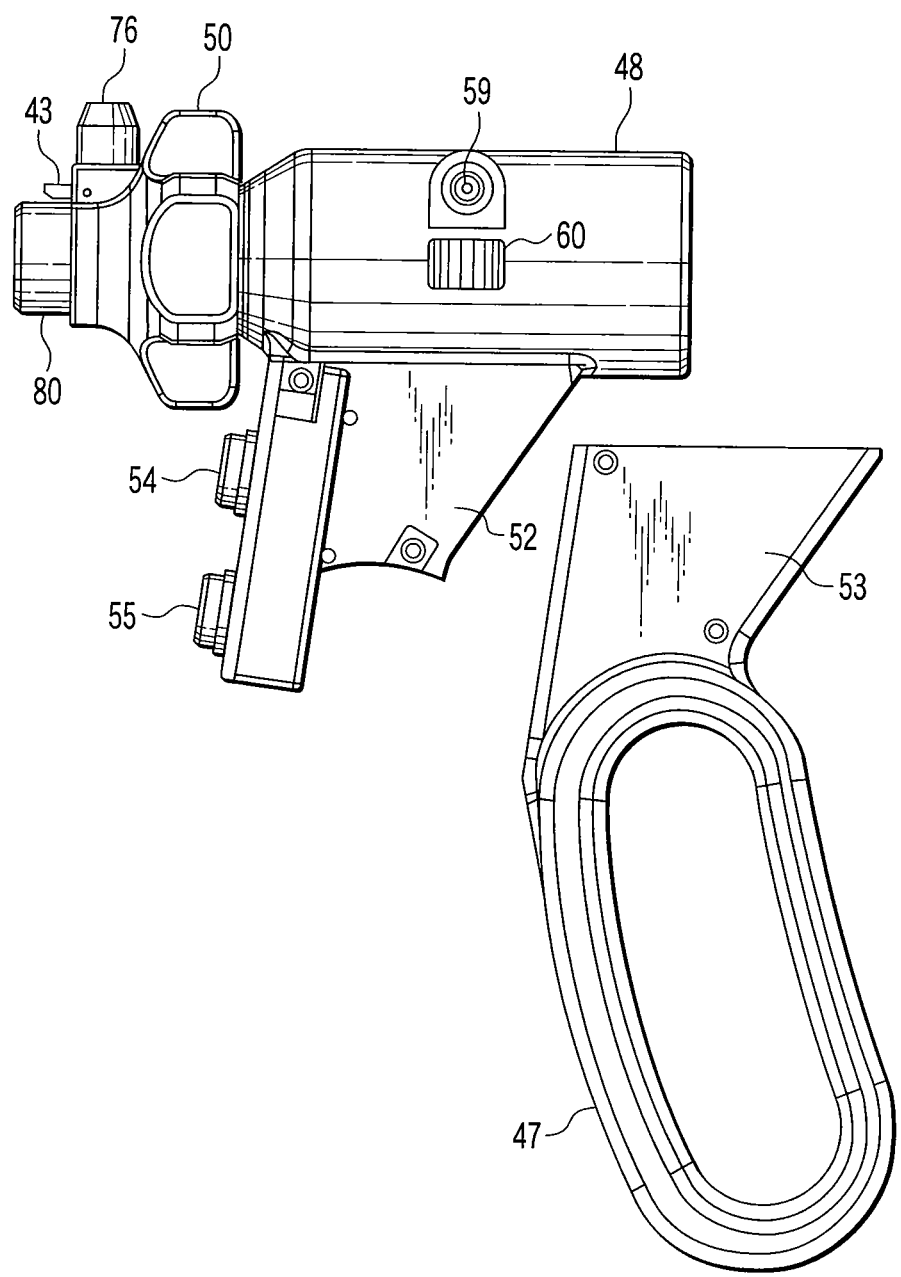
F I G. 35

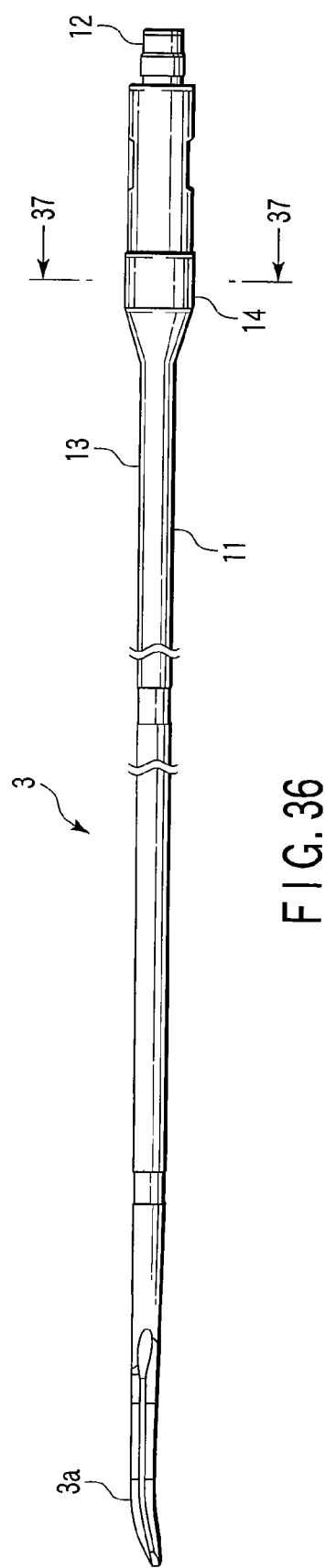
F I G. 36
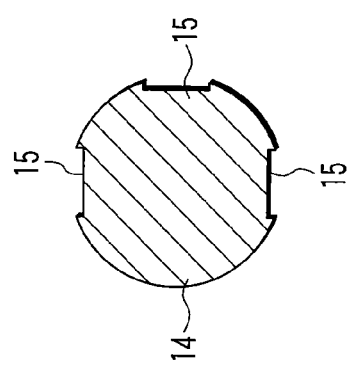
F I G. 37

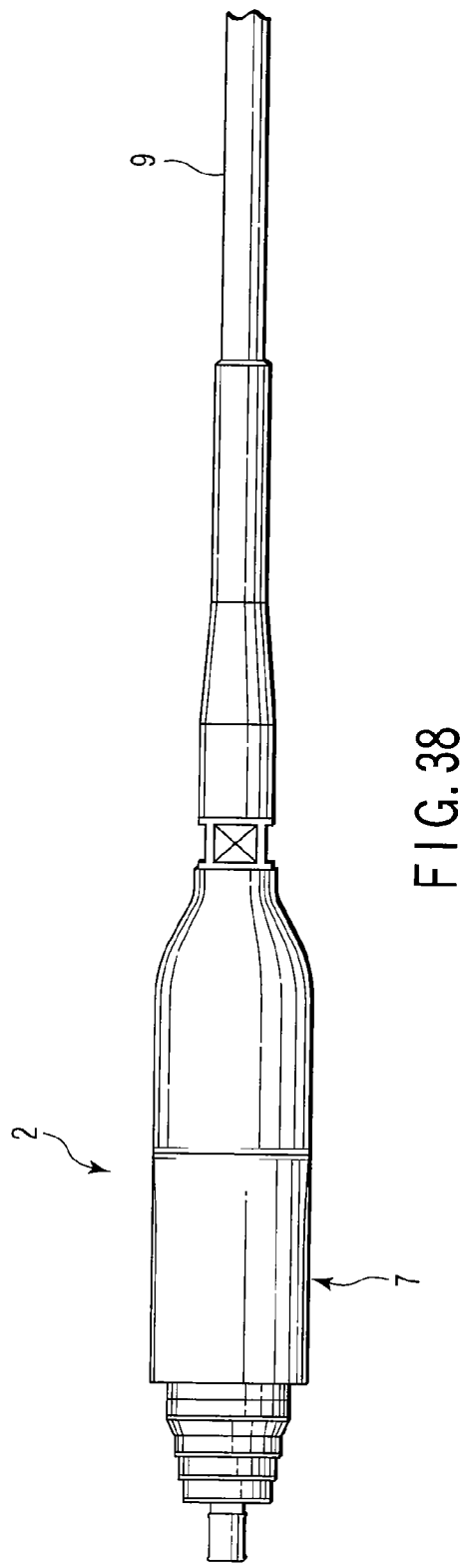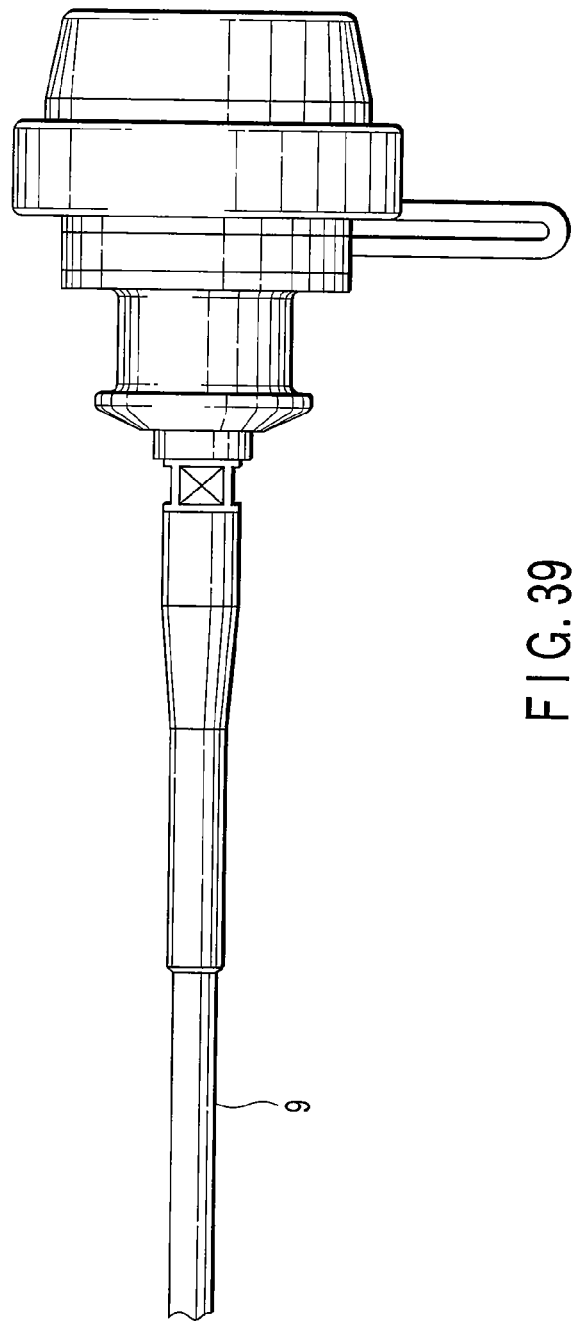
FIG. 38
FIG. 39

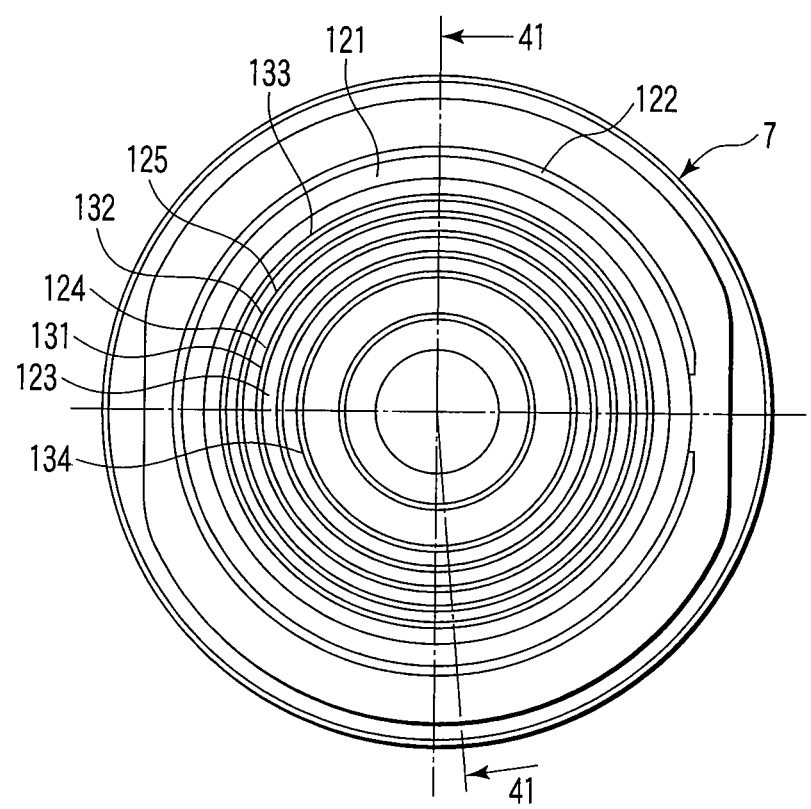
F I G. 40

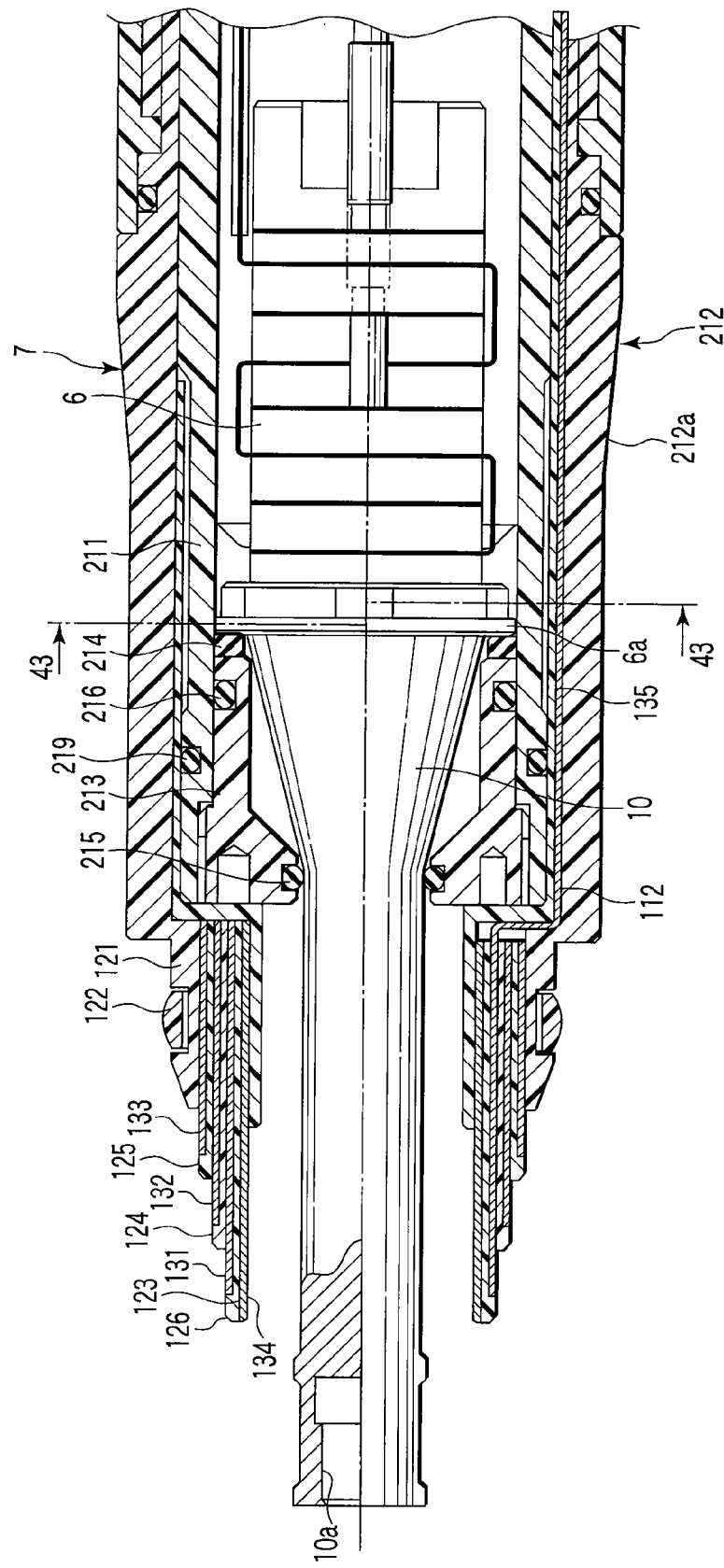
F I G. 41

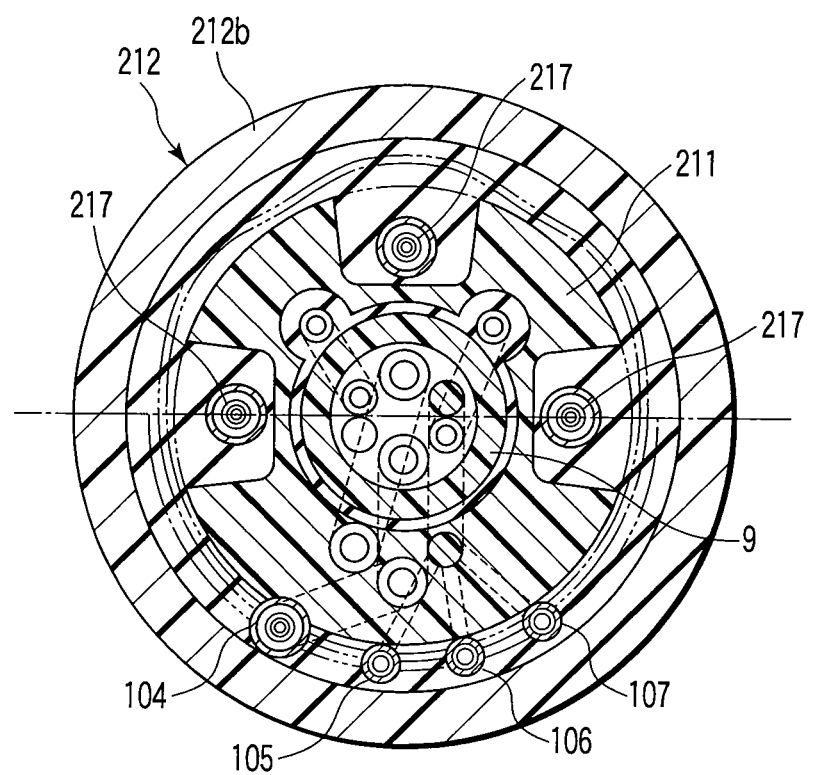
F I G. 45

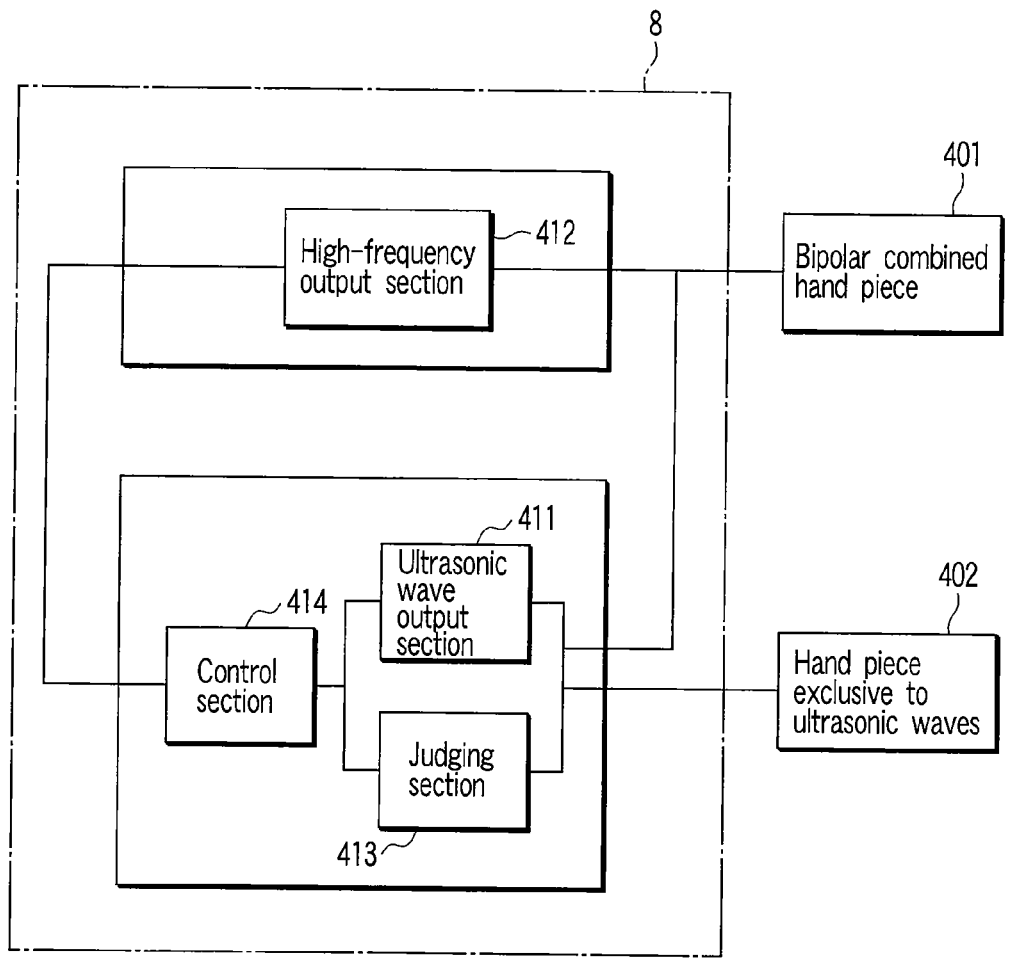
F I G. 49

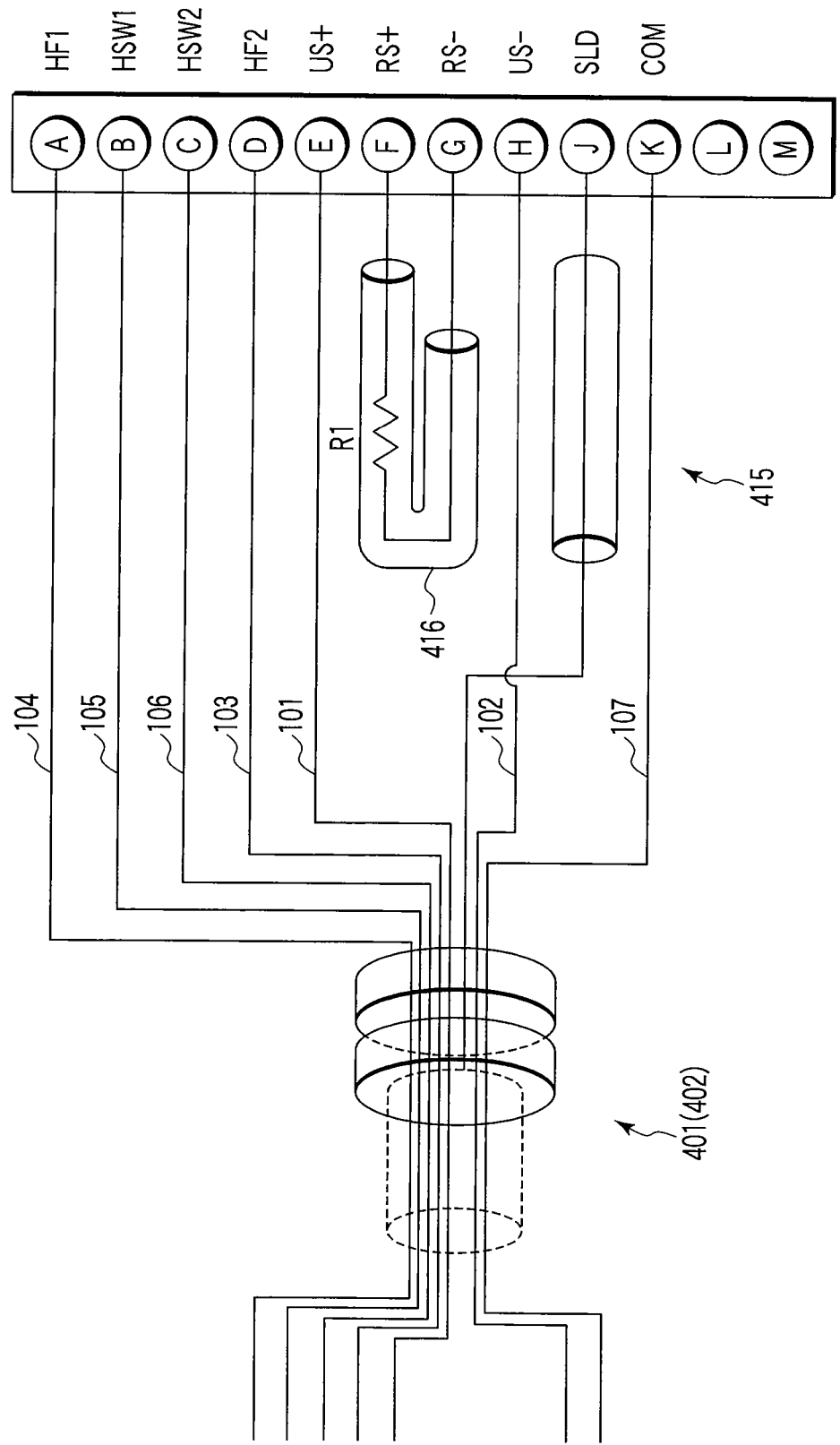
F I G. 50

ULTRASONIC OPERATING APPARATUS

BACKGROUND OF THE INVENTION

The present invention relates to an ultrasonic operating apparatus capable of a treatment such as incision, removal or coagulation of a living tissue by use of ultrasonic waves and also capable of a treatment with a high frequency.

An ultrasonic operating apparatus described in, for example, Jpn. Pat. Appln. KOKAI Publication No. 2005-118357 (Patent document 1) has been disclosed as one example of an ultrasonic operating apparatus generally capable of administering a treatment such as incision, removal or coagulation of a living tissue by use of ultrasonic waves and also capable of administering a treatment with a high frequency.

In this apparatus, an operation portion at hand is coupled to the proximal end of an elongate insertion portion. An ultrasonic transducer for generating ultrasonic vibrations is provided in this operation portion. A treatment portion for treating the living tissue is provided at the distal end of the insertion portion.

The insertion portion has an elongate circular tubular sheath. A vibration transmitting member is inserted in the sheath. The proximal end of the vibration transmitting member is detachably connected to the ultrasonic transducer via a threaded joint. Thus, the ultrasonic vibrations generated by the ultrasonic transducer are transmitted to an ultrasonic probe on the distal side of the vibration transmitting member. In this manner, the ultrasonic vibrations from the ultrasonic transducer are transmitted to the ultrasonic probe on the side of the treatment portion via the vibration transmitting member, thereby administering the treatment such as incision, removal or coagulation of the living tissue by use of the ultrasonic waves.

Furthermore, in the apparatus of Patent document 1 described above, the ultrasonic transducer is disposed within a transducer cover. The transducer cover has an inner casing and an outer casing. A heat insulating antivibration layer is formed between the inner casing and the outer casing.

Moreover, the operation portion is provided with a high-frequency output transmitting portion for transmitting a high-frequency output to the probe, and a switch attachment portion. In the switch attachment portion, there is disposed a switch for controlling the turning on/off of the high-frequency output. A high-frequency connecting pin is attached to the high-frequency output transmitting portion. An electric cord for supplying a high-frequency current from a high-frequency cauterization power supply unit is connected to the high-frequency connecting pin. The inner end of the high-frequency connecting pin is electrically connected to the ultrasonic probe of the treatment portion via the operation portion and via an electric conduction path within the sheath. Thus, the high-frequency current is supplied to the ultrasonic probe of the treatment portion as necessary, so that a high-frequency treatment such as the coagulation of the living tissue is administered.

Concerning the apparatus of Patent document 1 described above, there is also shown a configuration in which a switch unit having a switch for controlling an ultrasonic output is externally attached to the operation portion. One end of a connection cable for controlling the ultrasonic output is connected to the switch unit. A connection plug connected to the main unit of the ultrasonic operating apparatus is connected to the other end of this connection cable.

Furthermore, Jpn. Pat. Appln. KOKAI Publication No. 2002-330977 (Patent document 2) has disclosed an ultrasonic operating apparatus having a configuration in which an electric connection portion is provided within a hand piece. In this apparatus, an electric contact is disposed around an ultrasonic transducer incorporated in the hand piece. Another conducting member contacts this electric contact to connect electric paths when the hand piece is assembled.

BRIEF SUMMARY OF THE INVENTION

An ultrasonic operating apparatus in one aspect of the present invention comprises: an ultrasonic transducer which generates ultrasonic vibrations; a probe portion which has a distal end and a proximal end, the proximal end being coupled to the ultrasonic transducer, ultrasonic waves output from the ultrasonic transducer being transmitted to the probe portion; a storage portion which stores the ultrasonic transducer; a cylindrical casing portion which has a distal end and a proximal end and which is installed outside the storage portion; an electric path provided to extend between an electric contact disposed at the distal end of the casing portion and an electric cable connecting portion provided at the proximal end of the casing portion; and an electric cable which has a distal end and a proximal end, the proximal end being connected to a power supply unit, the distal end being coupled to the electric cable connecting portion, the electric path being disposed between the storage portion and the casing.

Preferably, the electric path has a plurality of electric path elements, and the plurality of electric path elements are provided side by side on diametrically equal parts of the outer peripheral surface of the transducer along a circumferential direction thereof.

Preferably, the plurality of electric path elements include at least one of electric path elements of a current for a hand switch and electric path elements of a current for a high-frequency treatment.

Preferably, the plurality of electric path elements are disposed in a direction different from the diametrical direction of the casing portion.

Preferably, the plurality of electric path elements are integrally molded to be buried in the casing portion.

Preferably, the electric contact has a stepped contact receiving portion which is disposed at the distal end of the casing portion and which is formed so that the outside diameter of the casing portion decreases stepwise toward a distal end side thereof, an outer peripheral surface side contact installed in the contact receiving portion disposed on the outer peripheral surface at the distal end of the casing, and an inner peripheral surface side contact disposed on the inner peripheral surface at the distal end of the casing.

An ultrasonic operating apparatus in another aspect of the present invention comprises: an ultrasonic transducer which generates ultrasonic vibrations; a probe portion which has a distal end and a proximal end, the proximal end being coupled to the ultrasonic transducer, ultrasonic waves output from the ultrasonic transducer being transmitted to the probe portion; a first high-frequency electric path which is provided in a combination of the ultrasonic transducer and the probe portion and which transmits a high-frequency current; a sheath portion which is formed by a cylindrical member having a distal end and a proximal end and into which the probe portion is removably inserted, the sheath portion having a jaw swingably supported on the distal end thereof to be opposite to the probe portion; a handle portion which is detachably coupled to the proximal end of the sheath portion and which opens/closes the jaw with respect to the probe portion, the handle portion having a transducer connecting portion to which the ultrasonic transducer is detachably connected, and a hand switch which selects a function of the probe portion; a second high-frequency electric path which is provided in a combination of the sheath portion and the handle portion and which transmits a high-frequency current; a storage portion which stores the ultrasonic transducer; a cylindrical casing portion which has a distal end and a proximal end and which is installed outside the storage portion; an electric cable which has a distal end and a proximal end, the proximal end being connected to a power supply unit, the distal end being coupled to the electric cable connecting portion, the electric cable having at least an electric wiring line for the ultrasonic transducer, a high-frequency conducting electric wiring line connected to the first and second high-frequency electric paths, and a hand switch electric wiring line connected to the hand switch; an electric cable connecting portion disposed at the proximal end of the casing portion, the electric cable connecting portion having at least a transducer electric connecting portion connected to the electric wiring line for the ultrasonic transducer, two high-frequency conducting electric connecting portions respectively connected to the first and second high-frequency electric wiring lines, and a hand switch electric connecting portion connected to the wiring line of the hand switch; and a contact disposition portion disposed at the distal end of the casing portion, the contact disposition portion having at least an electric contact connected to the second high-frequency electric path, and a hand switch electric contact connected to the hand switch, an electric path between the electric cable connecting portion and the contact disposition portion being disposed between the storage portion and the casing.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a perspective view showing a situation where coupling parts of the ultrasonic operating apparatus in the first embodiment are detached;

FIG. 3A is a plan view showing the distal end of a sheath unit of the ultrasonic operating apparatus in the first embodiment;

FIG. 3B is a plan view showing the distal end of a probe unit of the ultrasonic operating apparatus in the first embodiment;

FIG. 4A is a longitudinal sectional view showing the distal end of the sheath unit of the ultrasonic operating apparatus in the first embodiment;

FIG. 4B is a longitudinal sectional view showing an insulating coating on the inner peripheral surface of an inner cylinder;

FIG. 8 is a longitudinal sectional view showing the proximal end of the sheath unit of the ultrasonic operating apparatus in the first embodiment;

FIG. 9A is a sectional view along the IXA-IXA line in FIG. 8;

FIG. 9B is a sectional view along the IXB-IXB line in FIG. 8;

FIG. 21 is a sectional view along the 21-21 line in FIG. 16;
FIG. 22 is a sectional view along the 22-22 line in FIG. 16.

FIG. 29 is a perspective view showing an electrode member of the ultrasonic operating apparatus in the first embodiment;

FIG. 30 is a horizontal sectional view showing the electrode member of the ultrasonic operating apparatus in the first embodiment;

FIG. 35 is a side view showing a state before a set member is set to a base member of a fixed handle of the handle unit of the ultrasonic operating apparatus in the first embodiment;

FIG. 36 is a plan view showing the probe unit of the ultrasonic operating apparatus in the first embodiment;

FIG. 37 is a sectional view along the 37-37 line in FIG. 36;

FIG. 38 is a plan view showing how the transducer unit and a cable of the ultrasonic operating apparatus in the first embodiment are coupled together;

FIG. 39 is a plan view showing the proximal end of the transducer unit cable of the ultrasonic operating apparatus in the first embodiment;

FIG. 40 is a front view showing the distal end of the transducer unit of the ultrasonic operating apparatus in the first embodiment;

FIG. 41 is a sectional view along the 41-41 line in FIG. 40;

FIG. 45 is a sectional view along the 45-45 line in FIG. 42;

FIG. 49 is a schematic configuration diagram showing how a power supply main unit and hand pieces of the ultrasonic operating apparatus in a second embodiment of the present invention are connected together; and FIG. 50 is a schematic configuration diagram showing internal electric wiring lines of a connector portion provided in a cable of the hand piece of the ultrasonic operating apparatus in the second embodiment.

DETAILED DESCRIPTION OF THE INVENTION

Figure 1:
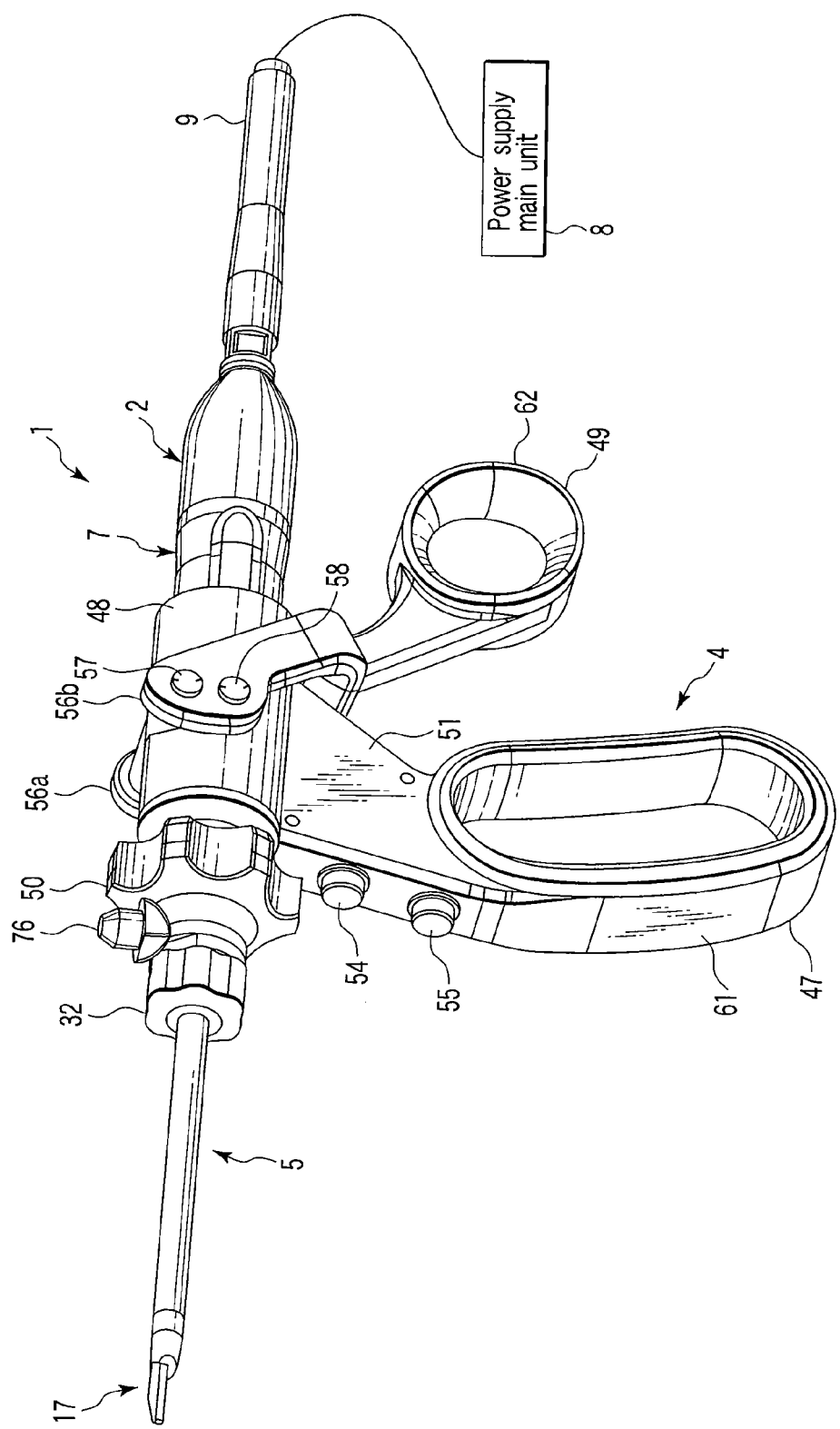
FIG. 1 is a perspective view showing an overall schematic configuration of an ultrasonic operating apparatus in a first embodiment of the present invention.
Figure 5:
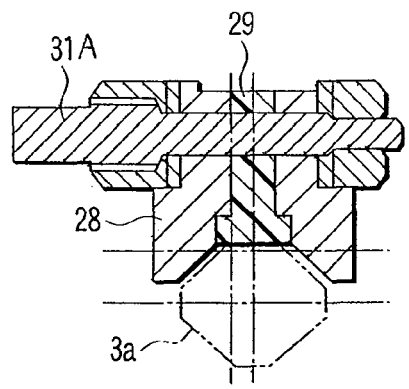
FIG. 5 is a sectional view along the V-V line in FIG. 4A.

Hereinafter, a first embodiment of the present invention will be described with reference to FIG. 1 to FIG. 48. FIG. 1 shows an overall schematic configuration of a hand piece 1 of an ultrasonic operating apparatus in the present embodiment. The ultrasonic operating apparatus in the present embodiment is an ultrasonic coagulation/incision operating apparatus capable of administering a treatment such as incision, removal or coagulation of a living tissue by use of ultrasonic waves and also capable of administering a treatment with a high frequency.

As shown in FIG. 2, the hand piece 1 has four units: a transducer unit 2, a probe unit (probe portion) 3, a handle unit (handle portion) 4, and a sheath unit (sheath portion) 5. These four units are removably coupled to each other.

In the transducer unit 2, there is incorporated a transducer 6 (see FIG. 41) described later for generating ultrasonic vibrations by a piezoelectric element which converts an electric current into the ultrasonic vibrations. The outside of the piezoelectric element is covered with a cylindrical transducer cover 7. Further, at the rear end of the transducer unit 2, a cable 9 extends to supply from a power supply main unit 8 an electric current for generating the ultrasonic vibrations.

The proximal end of a horn 10 for amplifying/expanding the ultrasonic vibrations is coupled to the front end of the ultrasonic transducer 6 within the transducer cover 7. A screw hole 10a for attaching a probe is formed at the distal end of the horn 10.

FIG. 36 shows an overall external appearance of the probe unit 3. This probe unit 3 is designed so that its entire length may be the integral multiple of the half-wave length of the ultrasonic vibrations. The probe unit 3 has a rod-like vibration transmitting member 11 made of a metal. A screw portion 12 for screwing into the screw hole 10a of the horn 10 is provided at the proximal end of the vibration transmitting member 11. Further, this screw portion 12 is threadably attached to the screw hole 10a of the horn 10 in the transducer unit 2. This sets the probe unit 3 and the transducer unit 2 together. At this point, a first high-frequency electric path 13 for transmitting a high-frequency current is formed in a combination of the ultrasonic transducer 6 and the probe unit 3.

A probe distal end 3a is provided at the distal end of the vibration transmitting member 11. The probe distal end 3a is formed to have a substantially J-shaped curve. The axial sectional area of the probe unit 3 is reduced at several vibration nodes partway in the axial direction so that amplitude necessary for a treatment can be obtained at the probe distal end 3a. Rubber rings formed of an elastic member with a ring shape are attached at several positions of the vibration nodes partway in the axial direction of the probe unit 3. Thus, these rubber rings prevent interference between the probe unit 3 and the sheath unit 5.

A flange portion 14 is provided at the position of the vibration node closest to the side of the proximal end in the axial direction of the probe unit 3. As shown in FIG. 37, keyway-shaped engaging concave portions 15 are formed on the outer peripheral surface of this flange portion 14 at three places in a circumferential direction.

Figure 7:
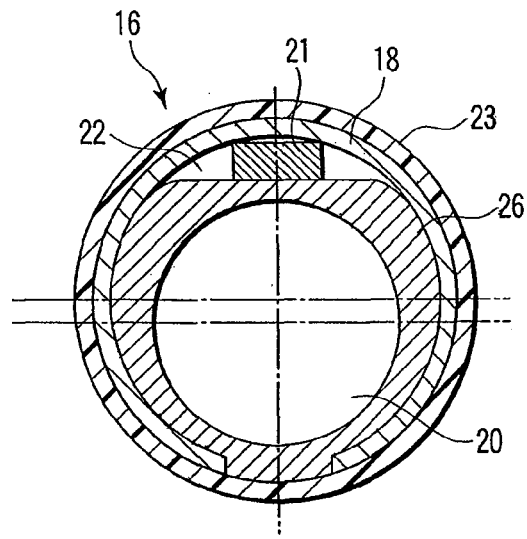
FIG. 7 is a sectional view along the VII-VII line in FIG. 4A.
Figure 10:
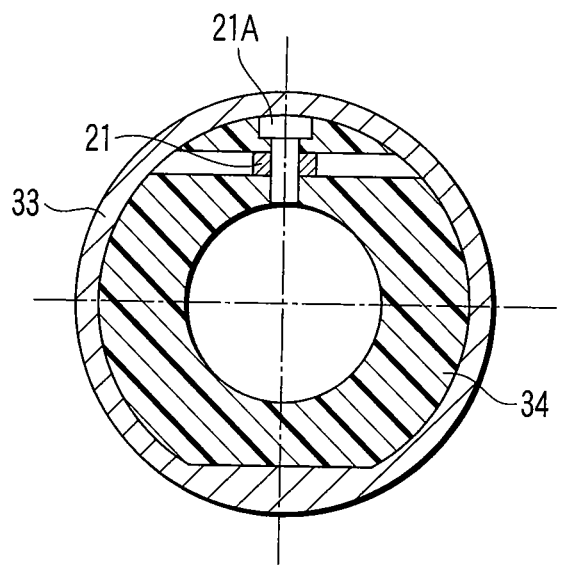
FIG. 10 is a sectional view along the X-X line in FIG. 8.
Figure 11:
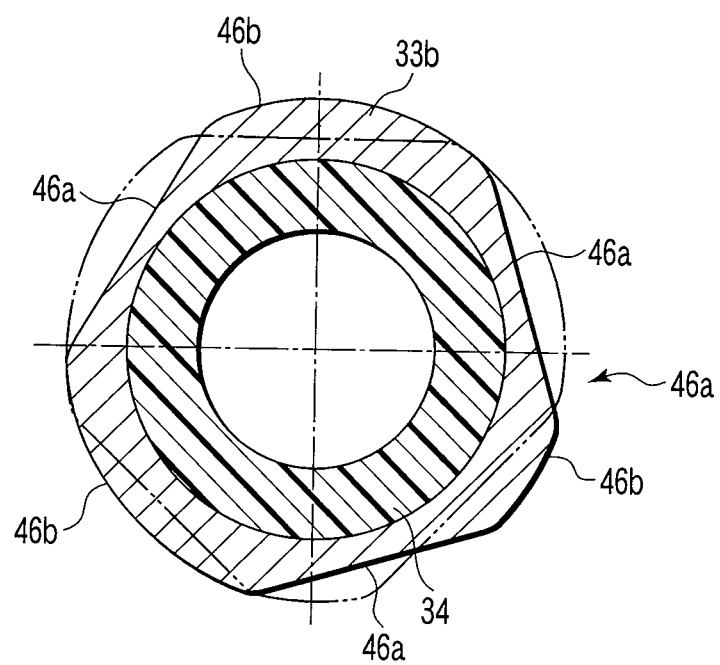
FIG. 11 is a sectional view along the XI-XI line in FIG. 8.

The sheath unit 5 has a sheath main body 16 formed by a cylindrical member, and a jaw 17 disposed at the distal end of the sheath main body 16. The sheath main body 16 has a metal outer cylinder 18 whose sectional shape is circular as shown in FIG. 7, and a metal inner cylinder 19 whose sectional shape is non-circular, for example, D-shaped. A channel 22 for passing a drive shaft 21 of the jaw 17 is formed between the outer cylinder 18 and the inner cylinder 19.

As shown in FIG. 4A, the outer peripheral surface of the outer cylinder 18 is covered with an insulating tube 23. As shown in FIG. 4B, an insulating coating 24 is formed by an insulating material on the inner peripheral surface of the inner cylinder 19. In addition, an insulating tube may be provided on the inner peripheral surface of the inner cylinder 19. Thus, the inner cylinder 19 is electrically insulated from the probe unit 3 by the insulating coating 24.

The proximal end of a substantially cylindrical distal end cover 25 is fixed to the distal end of the outer cylinder 18. On the side of the inner peripheral surface of the proximal end of the distal end cover 25, there is attached a pipe-shaped holding member 26 for holding the probe unit 3 to prevent this probe unit 3 from contacting the distal end cover 25. A channel 20 having a circular section for passing the probe unit 3 is formed inside the holding member 26.

Figure 6:
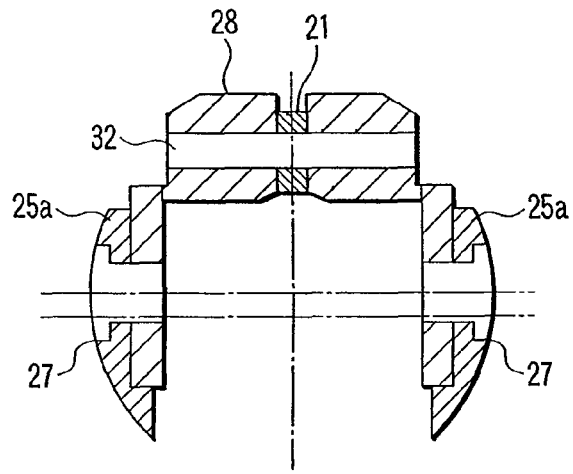
FIG. 6 is a sectional view along the VI-VI line in FIG. 4A.

As shown in FIG. 3A, a pair of right and left jaw support portions 25a is provided at the distal end of the distal end cover 25 to extend forward from the outer cylinder 18. A metal jaw main body 28 of the jaw 17 is swingably attached to these jaw support portions 25a via two supporting point pins 27, as shown in FIG. 6. This jaw 17 is formed to have a substantially J-shaped curve corresponding to the probe distal end 3a of the probe unit 3, as shown in FIG. 3A. Thus, the jaw 17 is opposite to the probe distal end 3a of the probe unit 3 and swingably supported on the two supporting point pins 27 (see FIG. 6). The jaw 17 is operated to swing between an open position at which the jaw 17 swings in a direction to move away from the probe distal end 3a of the probe unit 3 and a closing position at which the jaw 17 swings in a direction to approach the side of the probe distal end 3a of the probe unit 3. If the jaw 17 is operated to swing to the closing position, the living tissue is gripped between the jaw 17 and the probe distal end 3a of the probe unit 3.

The jaw main body 28 has a grip member 29 made of a resin such as PTFE, and a metal grip member attachment member 30 for holding the grip member 29. The grip member 29 is attached to the grip member attachment member 30 so that this grip member 29 can swing over a given angle by a pin 31A (see FIG. 5). Further, the distal end of the drive shaft 21 is coupled to the rear end of the jaw main body 28 via a pin 28a, as shown in FIG. 4A. This drive shaft 21 passes inside the distal end cover 25, and then passes between the outer cylinder 18 and the inner cylinder 19 of the sheath main body 16 as shown in FIG. 7, thus extending to the side of the proximal end of the sheath main body 16.

FIG. 8 shows the proximal end of the sheath main body 16. An attachment/detachment mechanism section 31 for attachment to/detachment from the handle unit 4 is provided at the proximal end of the sheath main body 16. The attachment/detachment mechanism section 31 has a cylindrical large-diameter pinch member 32 formed of a resin material, a guide cylindrical member 33 formed by a metal cylindrical member, and a cylindrical connecting pipe member 34 formed of a resin material.

The pinch member 32 has a first ring-shaped fixing portion 32a disposed at the front end, and a second cylindrical fixing portion 32b disposed at the rear end. The inner peripheral surface of the first fixing portion 32a is fixed to the outer peripheral surface of the proximal end of the sheath main body 16. The second fixing portion 32b of the pinch member 32 has a fixing portion 35 of the guide cylindrical member 33 disposed on the front end side, and a portion 36 disposed on the rear end side for attachment to/detachment from the handle unit 4.

The guide cylindrical member 33 has a large-diameter front end flange portion 33a disposed at the front end, and an outer peripheral flange portion 33b disposed on the rear end side. As shown in FIG. 9A, the front end flange portion 33a of the guide cylindrical member 33 is fixed to the pinch member 32 by two fixing screws 37 made of a resin while being inserted in the pinch member 32.

A metal joining pipe 38 is disposed inside the guide cylindrical member 33. The inner peripheral surface at the front end of this joining pipe 38 is fixed to the outer cylinder 18 of the sheath main body 16 by laser welding. Further, the joining pipe 38 is fixed to the guide cylindrical member 33 by a metal fixing screw 39. This permits electric conduction between the guide cylindrical member 33, the fixing screw 39, the joining pipe 38, the outer cylinder 18, the distal end cover 25, the supporting point pins 27 and the jaw main body 28, thereby forming a sheath unit side electric path 40 for transmitting a high-frequency current.

Figure 31:
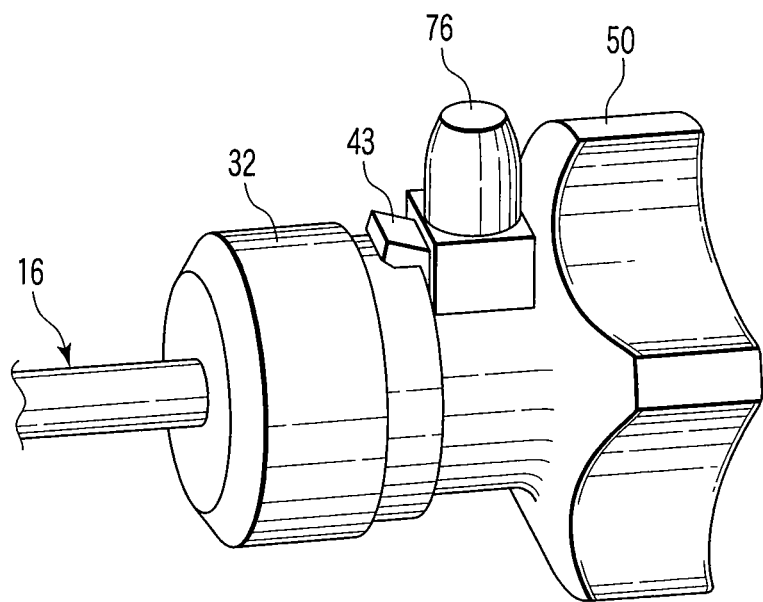
FIG. 31 is a perspective view showing a state before rotational engagement when the handle unit and the sheath unit of the ultrasonic operating apparatus in the first embodiment are coupled together.
Figure 32:
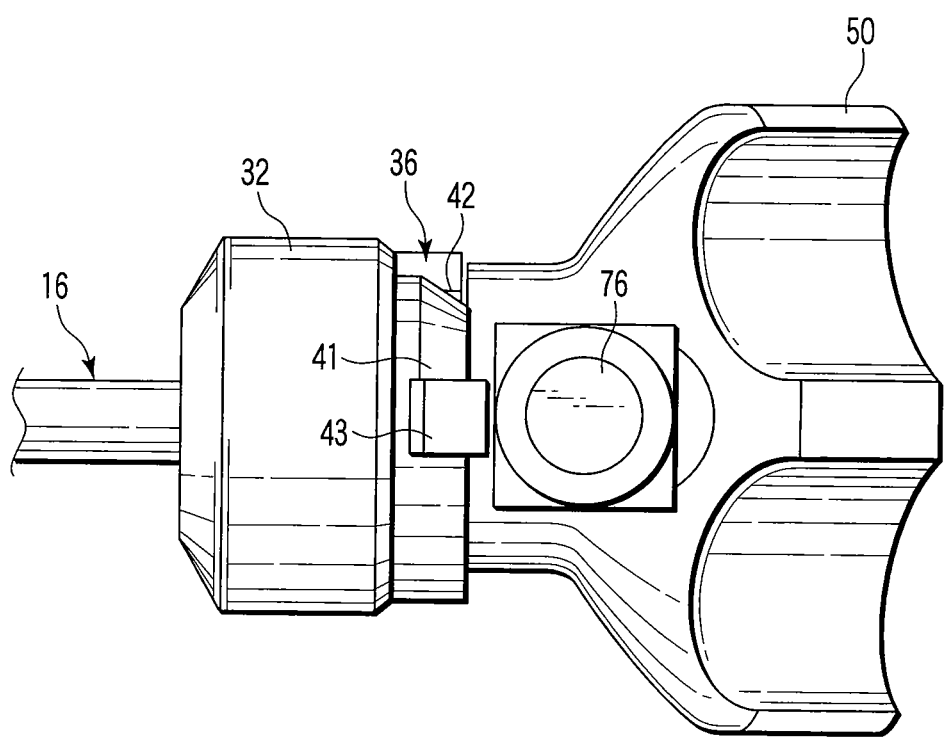
FIG. 32 is a plan view showing a state before rotational engagement when the handle unit and the sheath unit of the ultrasonic operating apparatus in the first embodiment are coupled together.
Figure 33:
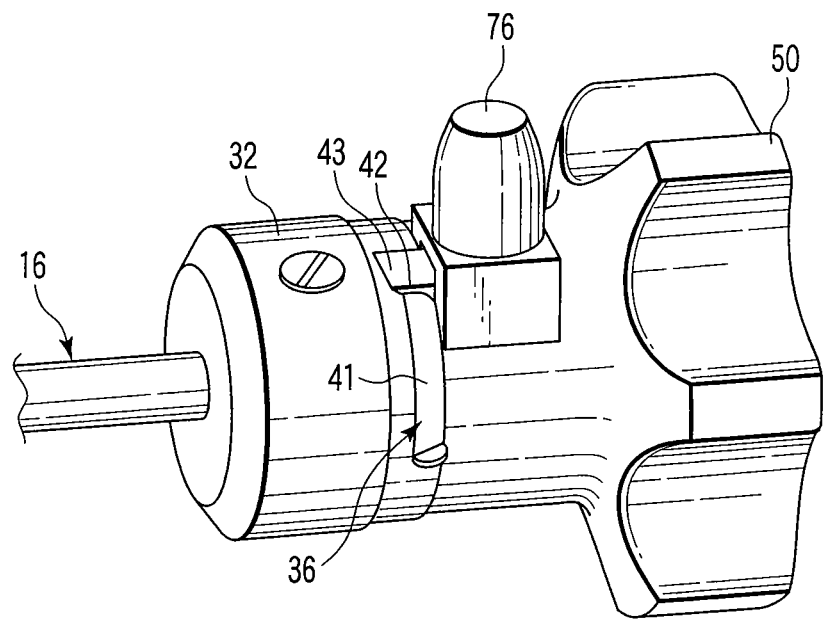
FIG. 33 is a perspective view showing a state after rotational engagement when the handle unit and the sheath unit of the ultrasonic operating apparatus in the first embodiment are coupled together.
Figure 34:
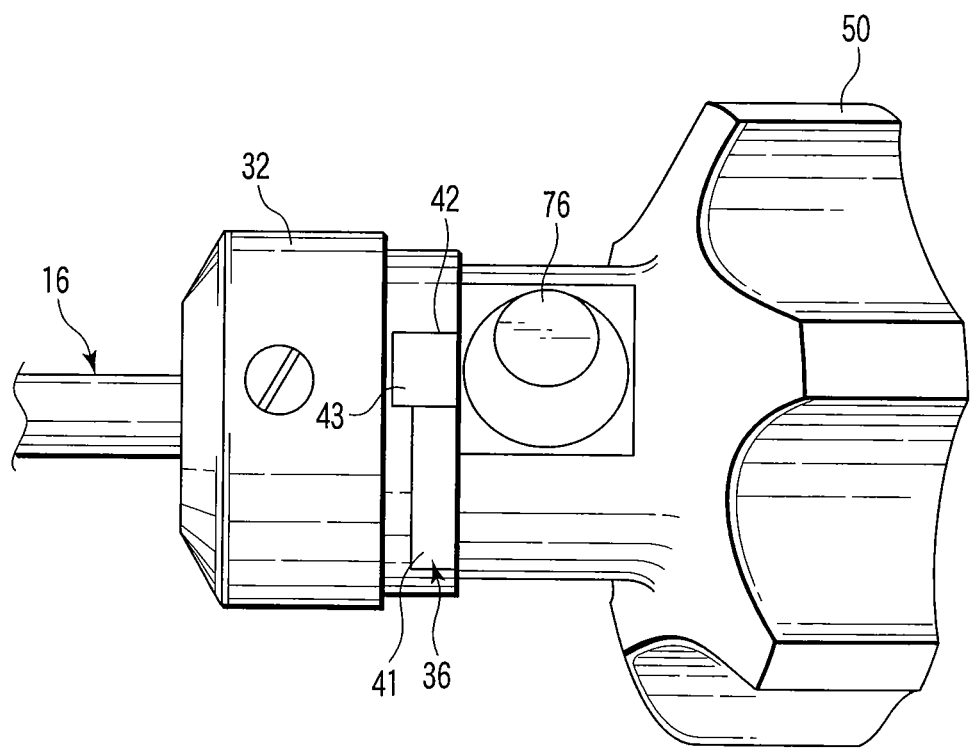
FIG. 34 is a plan view showing a state after rotational engagement when the handle unit and the sheath unit of the ultrasonic operating apparatus in the first embodiment are coupled together.

The attachment/detachment portion 36 of the pinch member 32 has a guide groove 41 in the form of an inclined surface provided to extend along a circumferential direction as shown in FIG. 9B, and an engaging concave portion 42 formed at one end of this guide groove 41. The guide groove 41 has a tapered inclined surface whose outside diameter becomes smaller as it approaches the side of the rear end of the pinch member 32. The engaging concave portion 42 is formed by a recessed portion whose diameter is smaller than that of the inclined surface of the guide groove 41. An engaging lever 43 described later on the side of the handle unit 4 removably engages with the engaging concave portion 42. FIGS. 33 and 34 show how the engaging lever 43 engages with the engaging concave portion 42, and FIGS. 31 and 32 show a disengaged state in which the engaging lever 43 is pulled out of the engaging concave portion 42.

Figure 12:
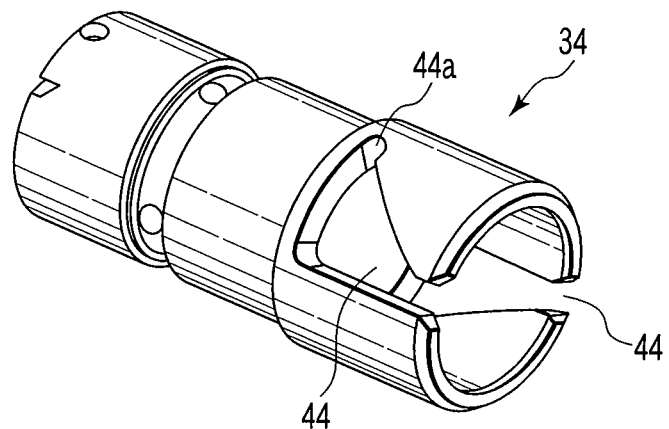
FIG. 12 is a perspective view showing a connecting pipe member of the sheath unit of the ultrasonic operating apparatus in the first embodiment.
Figure 13:
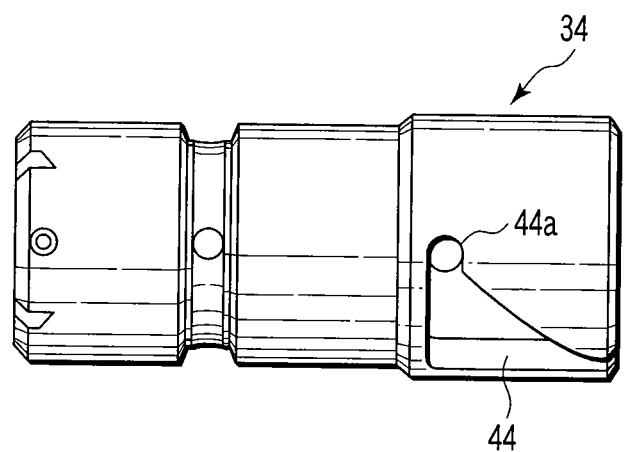
FIG. 13 is a side view showing the connecting pipe member of the sheath unit of the ultrasonic operating apparatus in the first embodiment.
Figure 14:
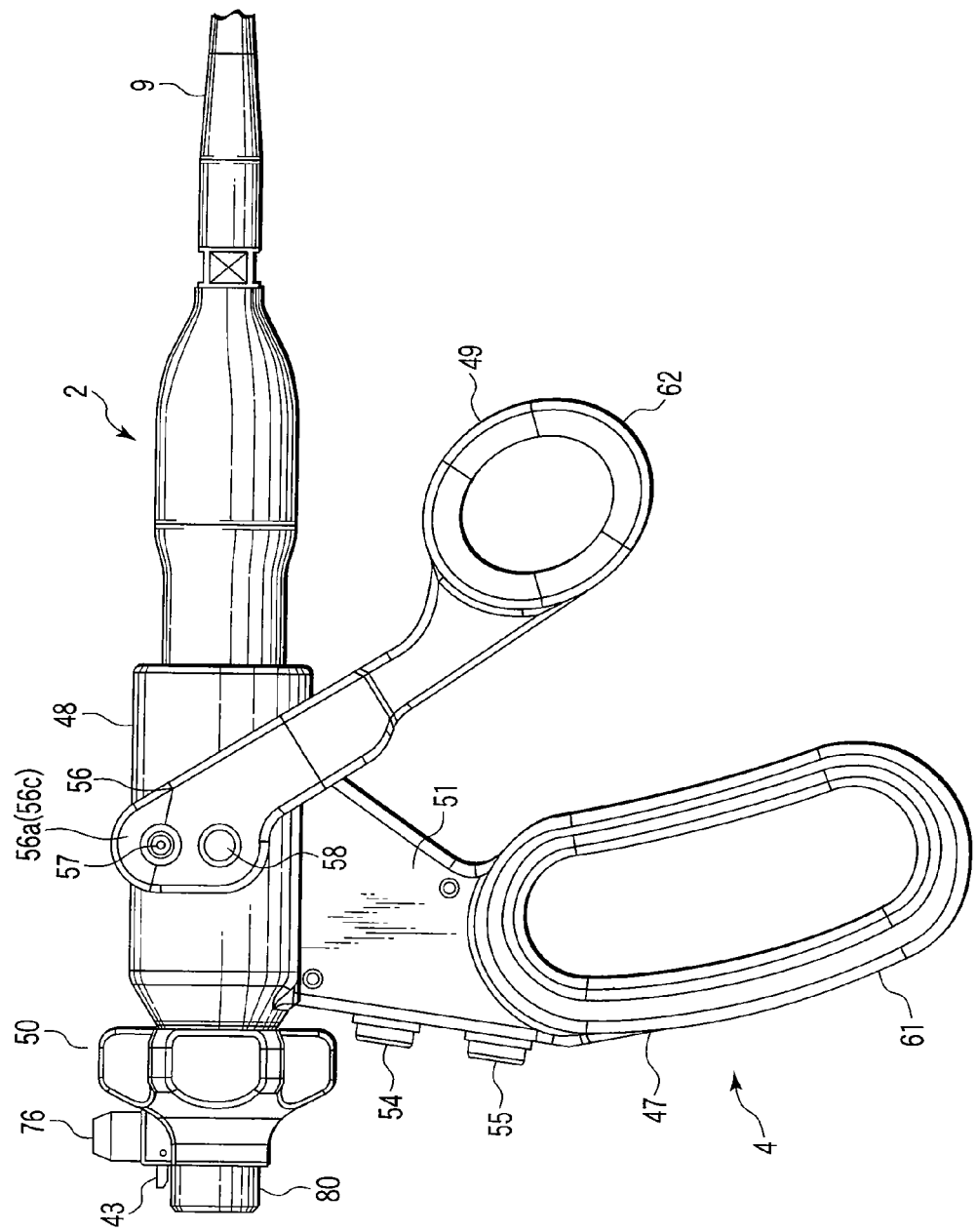
FIG. 14 is a side view showing how a handle unit and a transducer unit of the ultrasonic operating apparatus in the first embodiment are coupled together.
Figure 15:
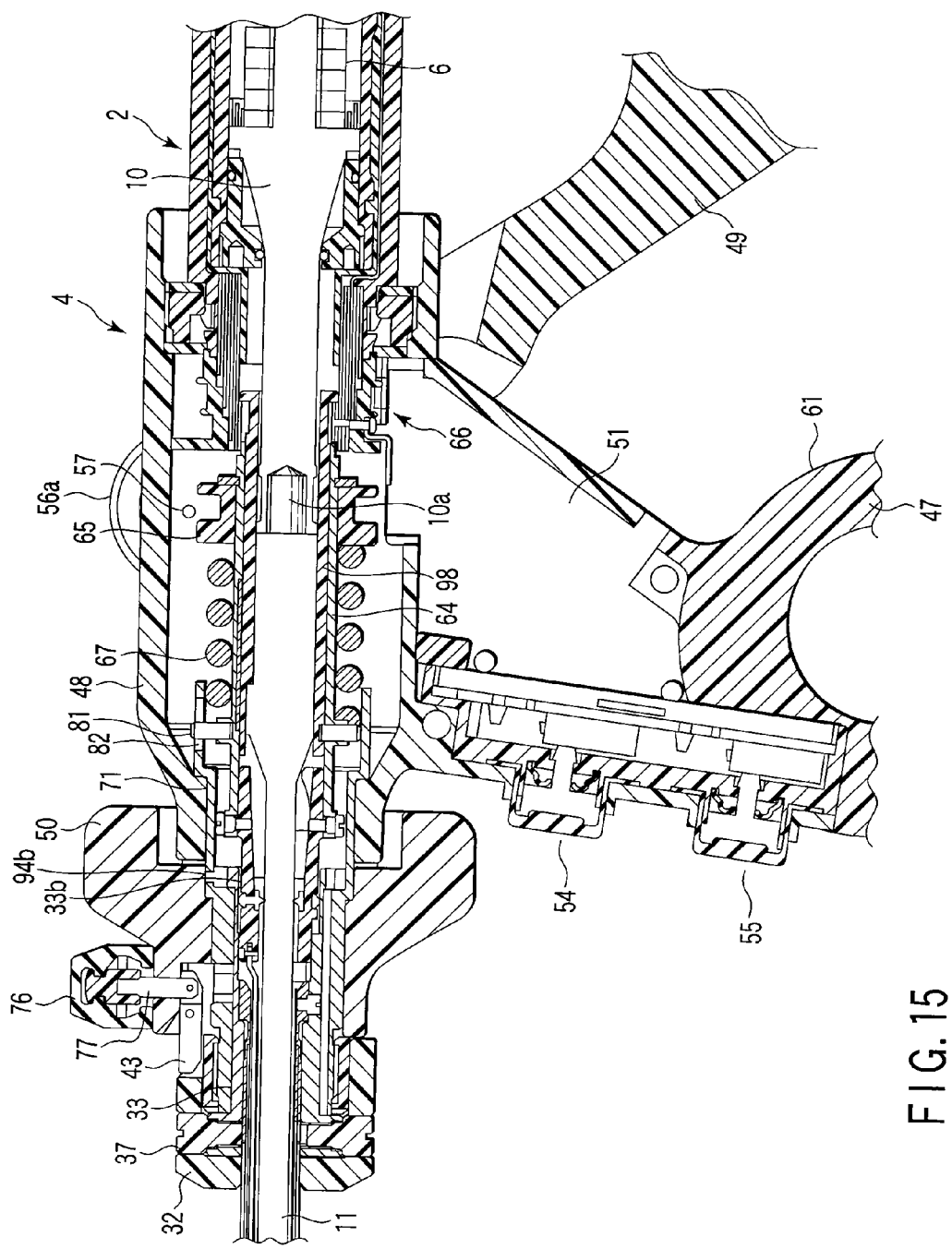
FIG. 15 is a longitudinal sectional view showing a unit coupling part of the ultrasonic operating apparatus in the first embodiment.

The connecting pipe member 34 is inserted into the guide cylindrical member 33 slidably in a direction of the axis line of the sheath main body 16. The proximal end of the drive shaft 21 is fixed to the distal end of this connecting pipe member 34 via a pin 21A (see FIG. 10). Two guide grooves 44 shown in FIGS. 12 and 13 are provided at the proximal end of the connecting pipe member 34. Engaging pins 45 described later on the side of the handle unit 4 removably engage with the guide grooves 44. At the terminal end of the guide groove 44, there is formed an engaging groove 44a which regulates the movement of the engaging pin 45 in the direction of the axis line of the sheath main body 16.

The outer peripheral flange portion 33b has a non-circular engaging portion 46. In the engaging portion 46, there are formed three plane portions 46a formed by cutting off a plurality of places, three places in the present embodiment, in the circular outer peripheral surface of the outer peripheral flange portion 33b. Corner portions 46b whose diameters are larger than those of the plane portions 46a are formed at junctions between the three plane portions 46a. Thus, the engaging portion 46 whose sectional shape is substantially close to a triangular shape is formed in the outer peripheral flange portion 33b. In addition, this non-circular engaging portion 46 does not necessarily have to have the substantially triangular shape, and various shapes including polygonal shapes such as quadrangular and pentangular shapes can be conceived as long as they are non-circular shapes.

The handle unit 4 mainly has a fixed handle 47, a holding cylinder 48, a movable handle 49, a swing operation knob 50, and a handle unit side electric path 95 for transmitting a high-frequency current. The holding cylinder 48 is disposed on the top of the fixed handle 47. A switch holding portion 51 is provided between the fixed handle 47 and the holding cylinder 48. As shown in FIG. 35, the switch holding portion 51 has a switch attachment portion 52 fixed to the lower end of the holding cylinder 48, and a cover member 53 fixed to the upper end of the fixed handle 47. The switch attachment portion 52 has a plurality of hand switch buttons, in the present embodiment, two hand switch buttons (e.g., a coagulation switch button 54 and an incision switch button 55) which are push button switches. In the switch attachment portion 52, there are incorporated a coagulation switch 54a operated by the coagulation switch button 54, an incision switch 55a operated by the incision switch button 55, and a wiring line circuit board 92.

To the wiring line circuit board 92, there are connected a coagulation wiring line 93a whose one end is connected to the coagulation switch 54a, an incision wiring line 93b whose one end is connected to the incision switch 55a, and a ground wiring line 93c whose one end is connected to a ground common terminal. These three wiring lines 93a to 93c are incorporated in the switch holding portion 51 in a rolled state.

Figure 20:
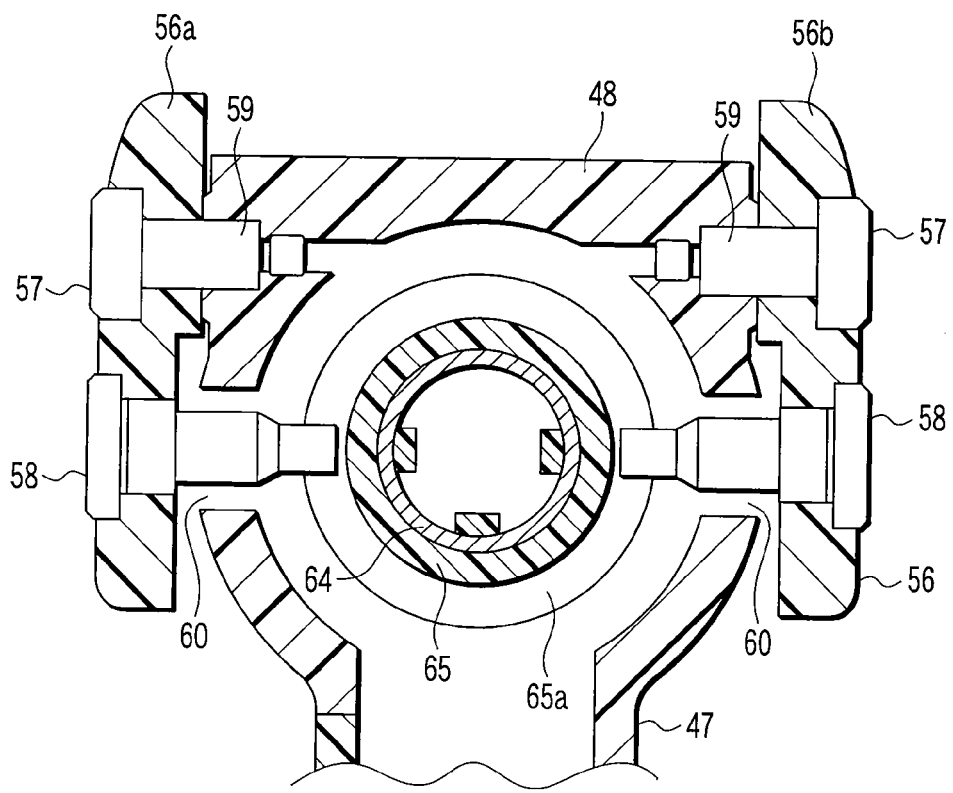
FIG. 20 is a sectional view along the 20-20 line in FIG. 16.

The movable handle 49 has a substantially U-shaped arm portion 56 on its top. The U-shaped arm portion 56 has two arms 56a and 56b, as shown in FIG. 20. The movable handle 49 is set to the holding cylinder 48 so that the holding cylinder 48 is inserted between the two arms 56a and 56b.

Each of the arms 56a and 56b has a supporting point pin 57 and an action pin 58. Pin receiving holes 59 and windows 60 are formed on both sides of the holding cylinder 48. The supporting point pin 57 of each of the arms 56a and 56b is inserted in the pin receiving hole 59 of the holding cylinder 48. Thus, the upper end of the movable handle 49 is swingably supported on the holding cylinder 48 via the supporting point pins 57.

Finger hooks 61 and 62 are provided at lower ends of the fixed handle 47 and the movable handle 49, respectively. Thus, the handles are gripped by fingers put on the finger hooks, such that the movable handle 49 swings via the supporting point pins 57, and the movable handle 49 opens/closes with respect to the fixed handle 47.

Each of the action pins 58 of the movable handle 49 extends into the holding cylinder 48 through the window 60 of the holding cylinder 48. An operation force transmitting mechanism 63 for transmitting the operation force of the movable handle 49 to the drive shaft 21 of the jaw 17 is provided inside the holding cylinder 48.

Figure 16:
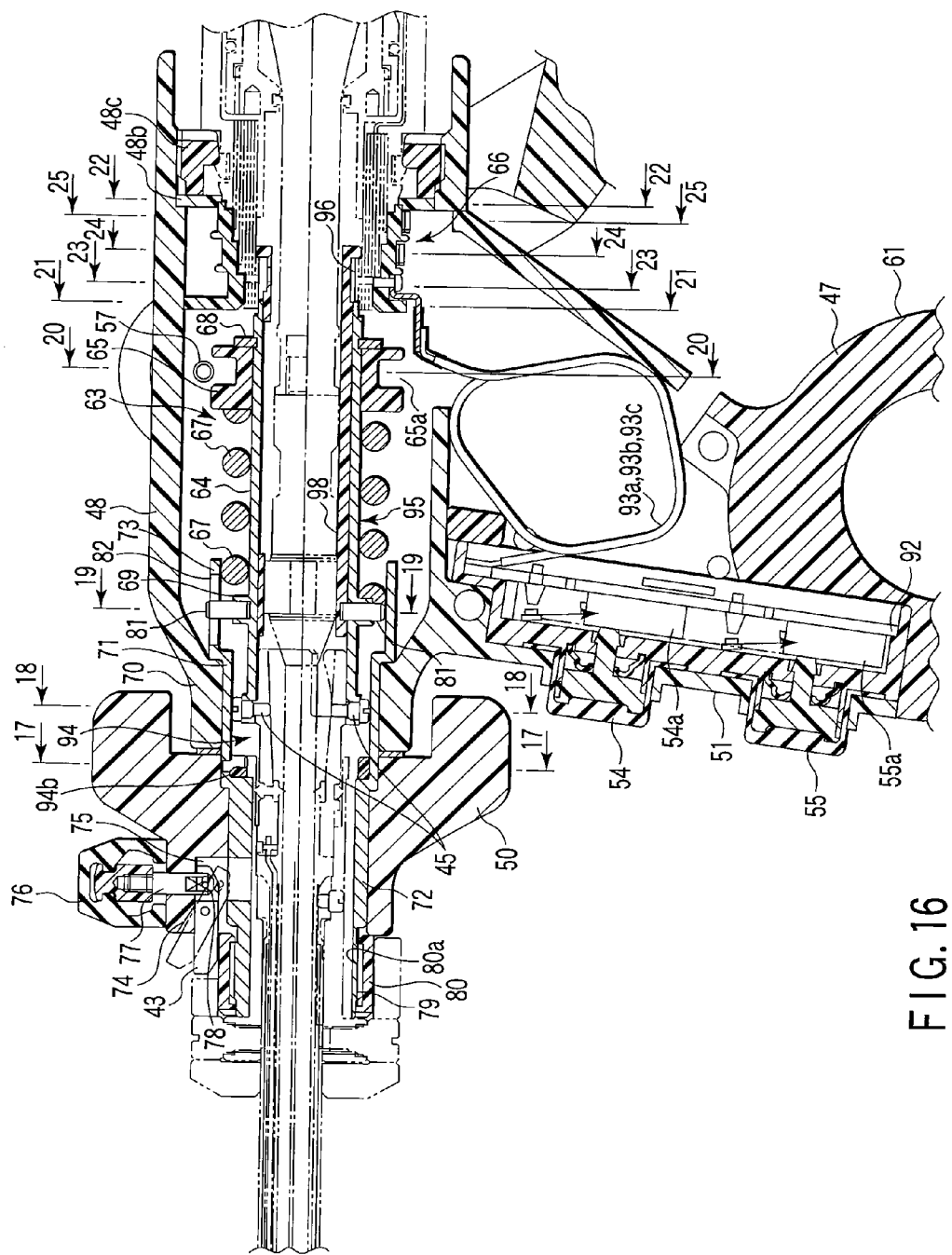
FIG. 16 is a longitudinal sectional view showing an internal configuration of the handle unit of the ultrasonic operating apparatus in the first embodiment.

As shown in FIG. 16, the operation force transmitting mechanism 63 has a cylindrical spring bearing member 64 mainly made of a metal, and a slider member 65 made of a resin. The spring bearing member 64 is disposed coaxially with the central line of the holding cylinder 48, and provided to extend in the same direction as the insertion direction of the probe unit 3.

The proximal end of the spring bearing member 64 is coupled to a later-described cylindrical contact unit 66 fixed to the proximal end of the holding cylinder 48 to be able to swing in a direction around the axis thereof and to be able to move back and forth in the same direction as the insertion direction of the probe unit 3. The pair of engaging pins 45 on the side of the handle unit 4 described above is provided to inwardly protrude at the distal end of the spring bearing member 64. When the handle unit 4 is coupled to the sheath unit 5, the pair of engaging pins 45 on the side of the handle unit 4 removably engages with the engaging grooves 44a at the terminal end of the guide grooves 44 of the sheath unit 5.

On the outer peripheral surface of the spring bearing member 64, there are provided a coil spring 67, the slider member 65, a stopper 68 and a spring bearing 69. The front end of the coil spring 67 is fixed to the spring bearing 69. The stopper 68 regulates the moving position of the rear end side of the slider member 65. The coil spring 67 is installed between the spring bearing 69 and the slider member 65 with a given amount of force of equipment.

A ring-shaped engaging groove 65a is formed on the outer peripheral surface of the slider member 65 along its circumferential direction. The action pins 58 of the movable handle 49 engage with the engaging groove 65a so that they are inserted in this engaging groove 65a, as shown in FIG. 20. Thus, when the movable handle 49 is gripped to close the movable handle 49 with respect to the fixed handle 47, the movable handle 49 swings so that the action pins 58 swing around the supporting point pins 57. The slider member 65 interlocked with the swing operation of the supporting point pins 57 moves forward along the axial direction. At this point, the spring bearing member 64 coupled to the slider member 65 via the coil spring 67 also moves back and forth together with the slider member 65. Thus, the operation force of the movable handle 49 is transmitted to the connecting pipe member 34 via the pair of engaging pins 45, and the drive shaft 21 of the jaw 17 moves forward. Therefore, the jaw main body 28 of the jaw 17 swings via the supporting point pins 27.

Furthermore, when the living tissue is gripped between the grip member 29 of the jaw 17 and the probe distal end 3a of the probe unit 3 in accordance with the above operation, the grip member 29 swings at a given angle on the pin 31A to follow the bending of the probe distal end 3a so that force is equally applied to the overall length of the grip member 29. When the ultrasonic waves are output in this state, it is possible to coagulate or incise the living tissue such as a blood vessel.

A ring-shaped bearing 70 is formed at the front end of the holding cylinder 48. A cylindrical rotation transmitting member 71 made of a metal is coupled to the bearing 70 swingably in a direction around the axis. In the rotation transmitting member 71, there are formed a protrusion 72 protruding ahead of the bearing 70, and a large-diameter portion 73 provided to extend from the bearing 70 onto the internal side of the holding cylinder 48.

The swing operation knob 50 is fixed to the protrusion 72 in an externally fitted state. The engaging lever 43 is provided at the front end of this swing operation knob 50. The intermediate portion of the engaging lever 43 is swingably coupled to the protrusion 72 via a pin 74. The proximal end of the engaging lever 43 extends into the inside of a lever receiving concave portion 75 formed in the front surface of the swing operation knob 50.

An operation button 76 for operating the engaging lever 43 in a disengaging direction is provided on the outer peripheral surface at the front end of the swing operation knob 50. A downward actuating pin 77 is provided to protrude in the operation button 76. The actuating pin 77 extends onto the internal side of the lever receiving concave portion 75 via a wall hole of the swing operation knob 50. The proximal end of the engaging lever 43 is coupled to the lower end of the actuating pin 77 via a pin 78.

A drop preventing ring 80 for the swing operation knob 50 is provided at the distal end of the protrusion 72. A male screw 79 is formed at the distal end of the protrusion 72. A female screw 80a to which the male screw 79 is threadably attached is formed on the inner peripheral surface of the drop preventing ring 80. Thus, the female screw 80a of the drop preventing ring 80 is screwed to the male screw 79 of the protrusion 72, such that the swing operation knob 50 is fixed to the rotation transmitting member 71.

Figure 19:
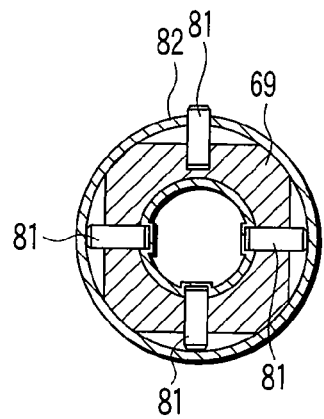
FIG. 19 is a sectional view along the 19-19 line in FIG. 16.

As shown in FIG. 19, four positioning pins 81 made of a metal are provided to diametrically outwardly protrude in the spring bearing 69 of the spring bearing member 64. A long-hole-shaped engaging hole 82 into which one pin 81 of the spring bearing member 64 is inserted is formed in the large-diameter portion 73 of the rotation transmitting member 71. The engaging hole 82 is provided to extend in the same direction as the insertion direction of the probe unit 3. Thus, the pin 81 is moved along the engaging hole 82 during the operation of the movable handle 49, thereby preventing the back-and-forth movement of the spring bearing member 64 from being transmitted to the rotation transmitting member 71.

On the contrary, the rotational operation of the rotation transmitting member 71 rotating together with the swing operation knob 50 is transmitted to the side of the spring bearing member 64 via the pin 81 during the rotational operation of the swing operation knob 50. Thus, during the rotational operation of the swing operation knob 50, a set unit including the rotation transmitting member 71, the pin 81, the spring bearing member 64, the slider member 65 and the coil spring 67 inside the holding cylinder 48 is driven to integrally rotate in a direction around the axis together with the swing operation knob 50.

Figure 26:
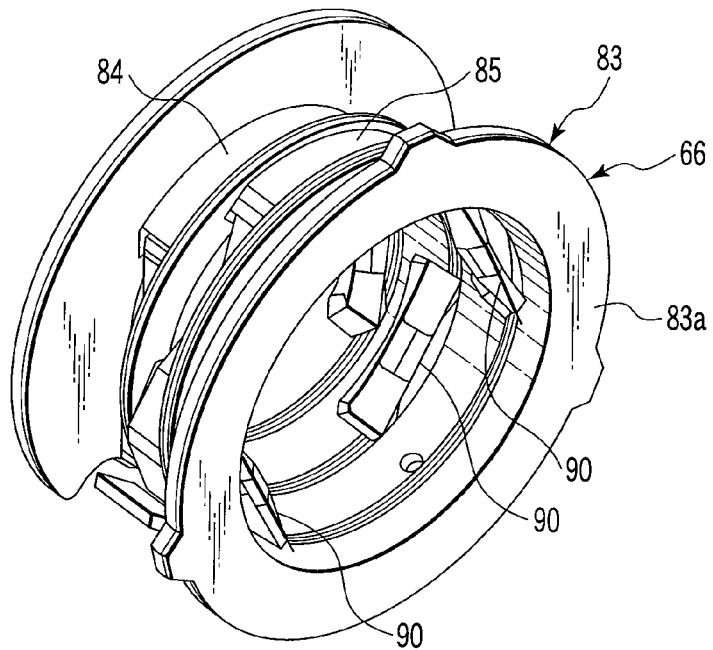
FIG. 26 is a perspective view showing an electrode holding member of the ultrasonic operating apparatus in the first embodiment.
Figure 27:
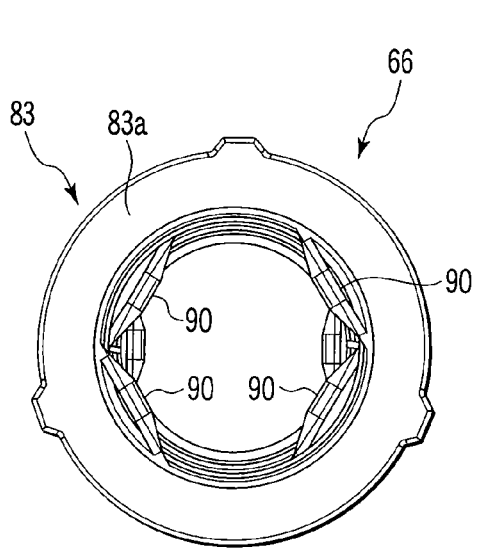
FIG. 27 is a front view showing the electrode holding member of the ultrasonic operating apparatus in the first embodiment.
Figure 28:
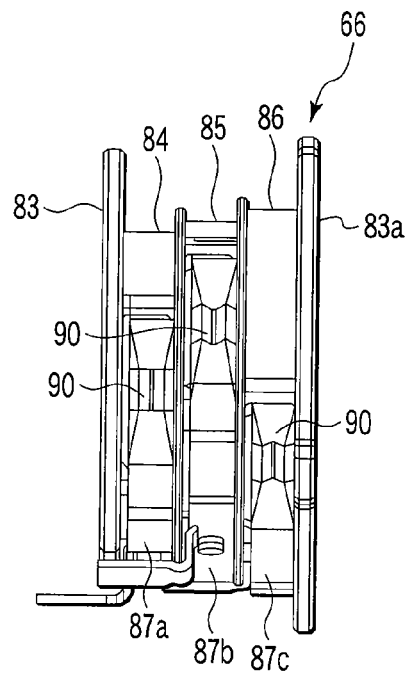
FIG. 28 is a side view showing the electrode holding member of the ultrasonic operating apparatus in the first embodiment.

FIGS. 26 to 28 show the cylindrical contact unit 66. The contact unit 66 has a cylindrical electrode holding member 83 made of a resin. The electrode holding member 83 has three (first to third) electrode receiving portions 84, 85 and 86 different in the size of outside diameter, as shown in FIG. 28. The first electrode receiving portion 84 on the distal end side has the smallest diameter, and the third electrode receiving portion 86 on the rear end side has the largest diameter.

Figure 23:
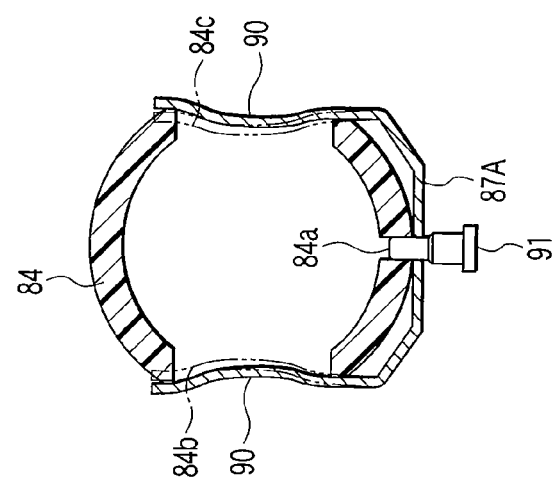
FIG. 23 is a sectional view along the 23-23 line in FIG. 16.

As shown in FIG. 23, the first electrode receiving portion 84 has one contact member fixing hole 84a and two through-holes 84b and 84c. The central lines of the two through-holes 84b and 84c are disposed at positions perpendicular to the central line of the contact member fixing hole 84a.

Figure 25:
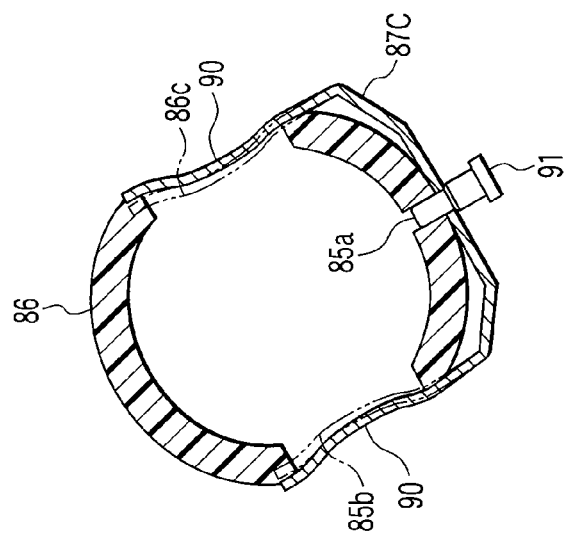
FIG. 25 is a sectional view along the 25-25 line in FIG. 16.
Figure 24:
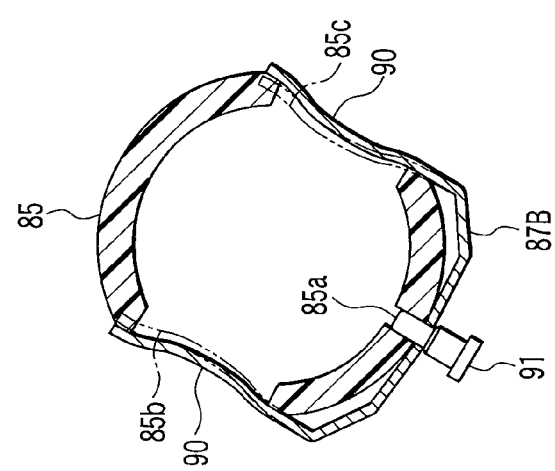
FIG. 24 is a sectional view along the 24-24 line in FIG. 16.

In the same manner, the second electrode receiving portion 85 has one contact member fixing hole 85a and two through-holes 85b and 85c, as shown in FIG. 24. The third electrode receiving portion 86 has one contact member fixing hole 86a and two through-holes 86b and 86c, as shown in FIG. 25.

The contact member fixing hole 84a of the first electrode receiving portion 84, the contact member fixing hole 85a of the second electrode receiving portion 85 and the contact member fixing hole 86a of the third electrode receiving portion 86 are positioned so that they are displaced from each other in the circumferential direction of the electrode holding member 83.

FIGS. 29 and 30 show electrode members 87A, 87B and 87C to be set to the first to third electrode receiving portions 84, 85 and 86. These electrode members 87A, 87B and 87C are formed to have the same shape. Here, the electrode member 87A to be set to the first electrode receiving portion 84 alone will be described, and the same signs are assigned to the same parts of the other electrode members 87B and 87C of the second and third electrode receiving portions 85 and 86, so that the electrode members 87B and 87C will not be described.

The electrode member 87A has one linear fixed portion 87a, and two bending portions 87b and 87c. The one bending portion 87b is disposed at one end of the linear fixed portion 87a, and the other bending portion 87c is disposed at the other end thereof. Thus, the electrode member 87A is formed to be bent into a substantially U shape, as shown in FIG. 29.

A hole 88 and an L-shaped wiring line connecting portion 89 are provided at the central position of the fixed portion 87a. Constricted portions 90 having an inwardly curving shape are formed in the two bending portions 87b and 87c at their central positions.

When the electrode member 87A is set to the first electrode receiving portion 84, a fixing pin 91 is inserted into the hole 88 of the fixed portion 87a of the electrode member 87A and into the contact member fixing hole 85a of the first electrode receiving portion 84. The electrode member 87A is fixed to the first electrode receiving portion 84 by the fixing pin 91. At this point, the constricted portion 90 of the one bending portion 87b of the electrode member 87A is disposed to be inserted into the one through-hole 85b of the first electrode receiving portion 84, while the constricted portion 90 of the other bending portion 87c of the electrode member 87A is disposed to be inserted into the other through-hole 85c. The same holds true for the case where the electrode member 87B is set to the second electrode receiving portion 85 and for the case where the electrode member 87C is set to the third electrode receiving portion 86.

As shown in FIG. 22, a large-diameter fixed flange portion 83a is formed at the rear end of the electrode holding member 83 of the contact unit 66. Engaging convex portions 83b are provided to protrude on the outer peripheral surface of the fixed flange portion 83a at a plurality of places, in the present embodiment, at three places. Engaging concave portions 48a are formed on the inner peripheral surface at the rear end of the holding cylinder 48 at positions corresponding to the three engaging convex portions 83b of the fixed flange portion 83a. When the electrode holding member 83 is set to the holding cylinder 48, they are engaged with and fixed to each other so that the three engaging convex portions 83b of the fixed flange portion 83a are inserted into the engaging concave portions 48a of the holding cylinder 48. This regulates the rotation of the electrode holding member 83 with respect to the holding cylinder 48 in the direction around the axis.

A step portion 43b for contacting the fixed flange portion 83a of the electrode holding member 83 is formed in the holding cylinder 48. The electrode holding member 83 is screwed to the holding cylinder 48 by a fixing screw 48c so that the fixed flange portion 83a of the electrode holding member 83 is placed in collision with this step portion 43b. This regulates the axial movement of the electrode holding member 83 with respect to the holding cylinder 48.

The ends of three wiring lines 93a to 93c incorporated in the switch holding portion 51 are connected to the wiring line connecting portions 89 of the three electrode members 87A, 87B and 87C set to the contact unit 66.

The contact unit 66 is further provided with a substantially C-shaped electric contact member 96 configured by a metal leaf spring, as shown in FIG. 21. The electric contact member 96 is connected to the outer peripheral surface at the proximal end of the spring bearing member 64.

The handle unit side electric path 95 comprises the electric contact member 96, the spring bearing member 64, the positioning pins 81 and the rotation transmitting member 71.

Figure 17A:
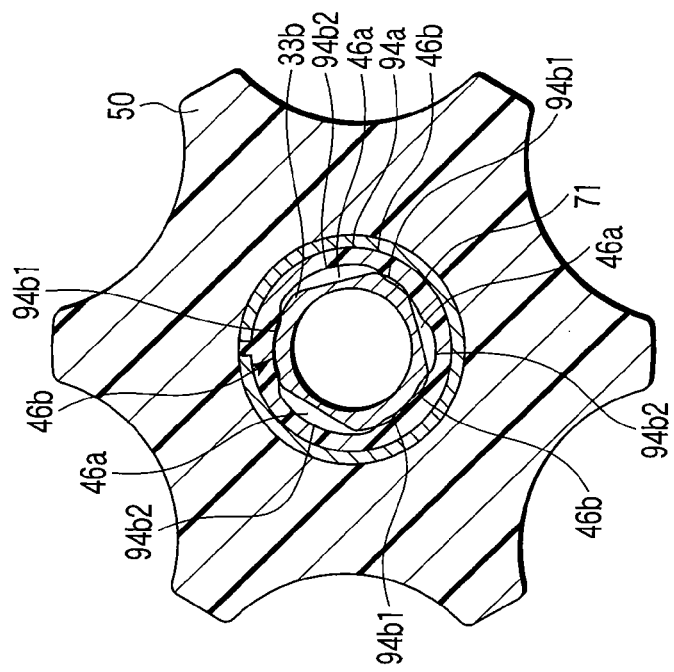
FIG. 17A is a sectional view along the 17-17 line in FIG. 16 showing a state before engagement between the handle unit and the sheath unit of the ultrasonic operating apparatus in the first embodiment.
Figure 17B:
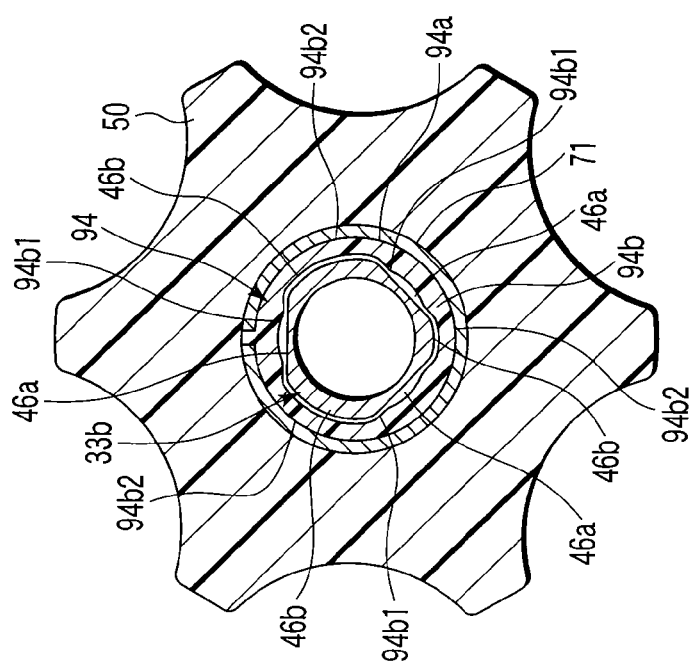
FIG. 17B is a sectional view along the 17-17 line in FIG. 16 showing a state after engagement between the handle unit and the sheath unit of the ultrasonic operating apparatus in the first embodiment.
Figure 18:
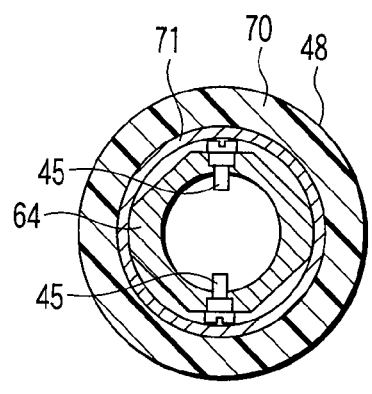
FIG. 18 is a sectional view along the 18-18 line in FIG. 16.

On the inner peripheral surface of the rotation transmitting member 71, there is provided engaging means 94 for removably engaging with the outer peripheral flange portion 33b of the sheath unit 5 substantially at the central position along the axial direction. As shown in FIGS. 17A and 17B, this engaging means 94 has an insertion hole 94a into which the outer peripheral flange portion 33b is inserted when the sheath unit 5 is coupled to the handle unit 4, and a conductive rubber ring (urging means) 94b disposed in the insertion hole 94a.

The shape of the inner peripheral surface of the conductive rubber ring 94b is substantially the same as that of the engaging portion 46 of the outer peripheral flange portion 33b. In other words, there are formed three plane portions 94b1 cut at a plurality of places, in the present embodiment, at three places on the circular inner peripheral surface, and three corner portions 94b2 which are disposed at junctions between the three plane portions 94b1 and which have diameters larger than those of the plane portions 94b1. This forms a sectional shape substantially close to a triangular shape. Therefore, the conductive rubber ring 94b is held at a non-compression position where it is in a natural state, at a position where the shape of the inner peripheral surface of the conductive rubber ring 94b corresponds to the engaging portion 46 of the outer peripheral flange portion 33b, that is, in a situation where the three corner portions 46b of the outer peripheral flange portion 33b correspond to the three corner portions 94b2 of the conductive rubber ring 94b, as shown in FIG. 17A. On the contrary, if the handle unit 4 and the sheath unit 5 are rotated relatively to each other in the direction around the central axis of the sheath unit 5, the conductive rubber ring 94b is switched to a pressure-contact position at which the conductive rubber ring 94b is brought into pressure-contact with the three corner portions 46b of the outer peripheral flange portion 33b, as shown in FIG. 17B. At this point, the three corner portions 46b of the outer peripheral flange portion 33b contact the three plane portions 94b1 of the conductive rubber ring 94b, and are thus compressed.

In the present embodiment, the conductive rubber ring 94b is held at the non-compression position where it is in the natural state as shown in FIG. 17A during an insertion operation (see FIGS. 31 and 32) in which the outer peripheral flange portion 33b of the sheath unit 5 is inserted straight into the conductive rubber ring 94b when the sheath unit 5 is coupled to the handle unit 4. At this point, the engaging lever 43 on the side of the handle unit 4 is held while being stranded on the inclined surface of the guide groove 41 of the pinch member 32 of the sheath unit 5. Then, the pinch member 32 of the sheath unit 5 is rotated with respect to the handle unit 4 in a direction around the axis, such that the engaging lever 43 on the side of the handle unit 4 engages in an inserted state with the engaging concave portion 42 at one end of the guide groove 41, as shown in FIGS. 33 and 34. At this point, the conductive rubber ring 94b is switched to a pressure-contact position at which the conductive rubber ring 94b is brought into pressure-contact with the three corner portions 46b of the outer peripheral flange portion 33b, as shown in FIG. 17B. This permits conduction, via the conductive rubber ring 94b, between the sheath unit side electric path 40 and the handle unit side electric path 95. At this point, a second high-frequency electric path 97 for transmitting a high-frequency current is formed in a combination of the sheath unit 5 and the handle unit 4.

As shown in FIG. 21, the handle unit 4 has a tubular member 98 formed by an insulating material on the inner peripheral surface of the spring bearing member 64. The tubular member 98 is fixed to the inner peripheral surface of the spring bearing member 64. Thus, the tubular member 98 provides insulation between the first high-frequency electric path 13 and the second high-frequency electric path 97 when the probe unit 3 is connected to the handle unit 4.

On the inner peripheral surface of the tubular member 98, there are formed three engaging convex portions 99 corresponding to the three engaging concave portions 15 (see FIG. 37) of the flange portion 14 of the probe unit 3. When the probe unit 3 is connected to the handle unit 4, the three engaging convex portions 99 of the tubular member 98 removably engage with the three engaging concave portions 15 of the flange portion 14 of the probe unit 3. This regulates the positions of the probe unit 3 and the tubular member 98 of the handle unit 4 in the rotation direction. Thus, a combination of the probe unit 3 and the transducer unit 2 is driven to integrally rotate together with a set unit inside the holding cylinder 48 during the rotational operation of the swing operation knob 50.

In addition, the engaging portion between the flange portion 14 of the probe unit 3 and the tubular member 98 is not limited to the configuration described above. For example, the tubular member 98 may be formed to have a D-shaped section, and the flange portion 14 of the probe unit 3 may be formed to have a D-shaped section correspondingly.

Figure 48:
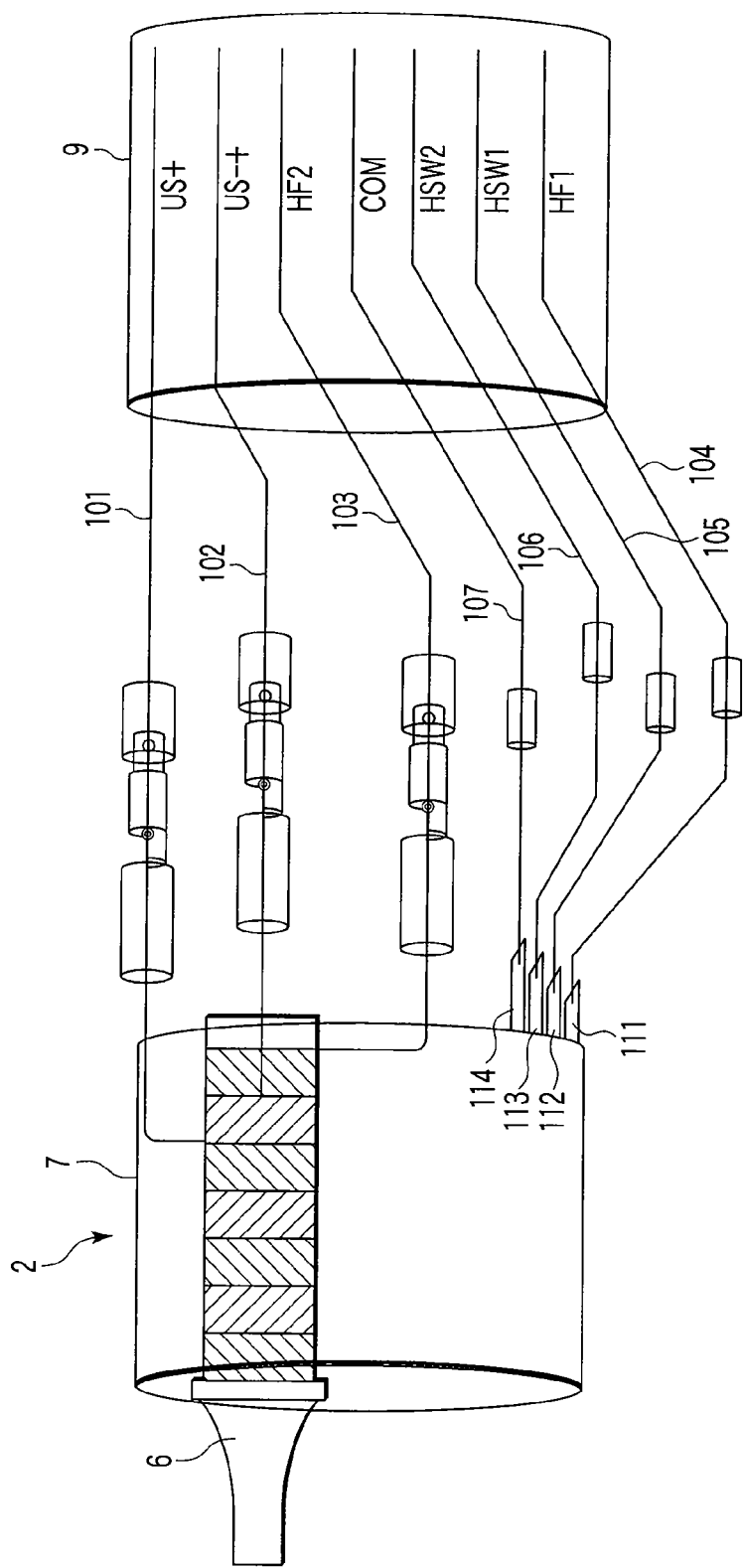
FIG. 48 is a schematic configuration diagram showing electric paths of the transducer unit of the ultrasonic operating apparatus in the first embodiment.

The front end of the transducer unit 2 is removably coupled to the contact unit 66. In one cable 9 at the rear end of the transducer unit 2, there are incorporated two wiring lines 101 and 102 for the ultrasonic transducer, two wiring lines 103 and 104 for high-frequency conduction, and three wiring lines 105, 106 and 107 connected to the wiring line circuit board 92 within the switch holding portion 51, as shown in FIG. 48. The distal ends of the two wiring lines 101 and 102 for the ultrasonic transducer are connected to the ultrasonic transducer 6. The distal end of the one wiring line 103 for the high-frequency conduction is connected to the ultrasonic transducer 6.

Figure 42:
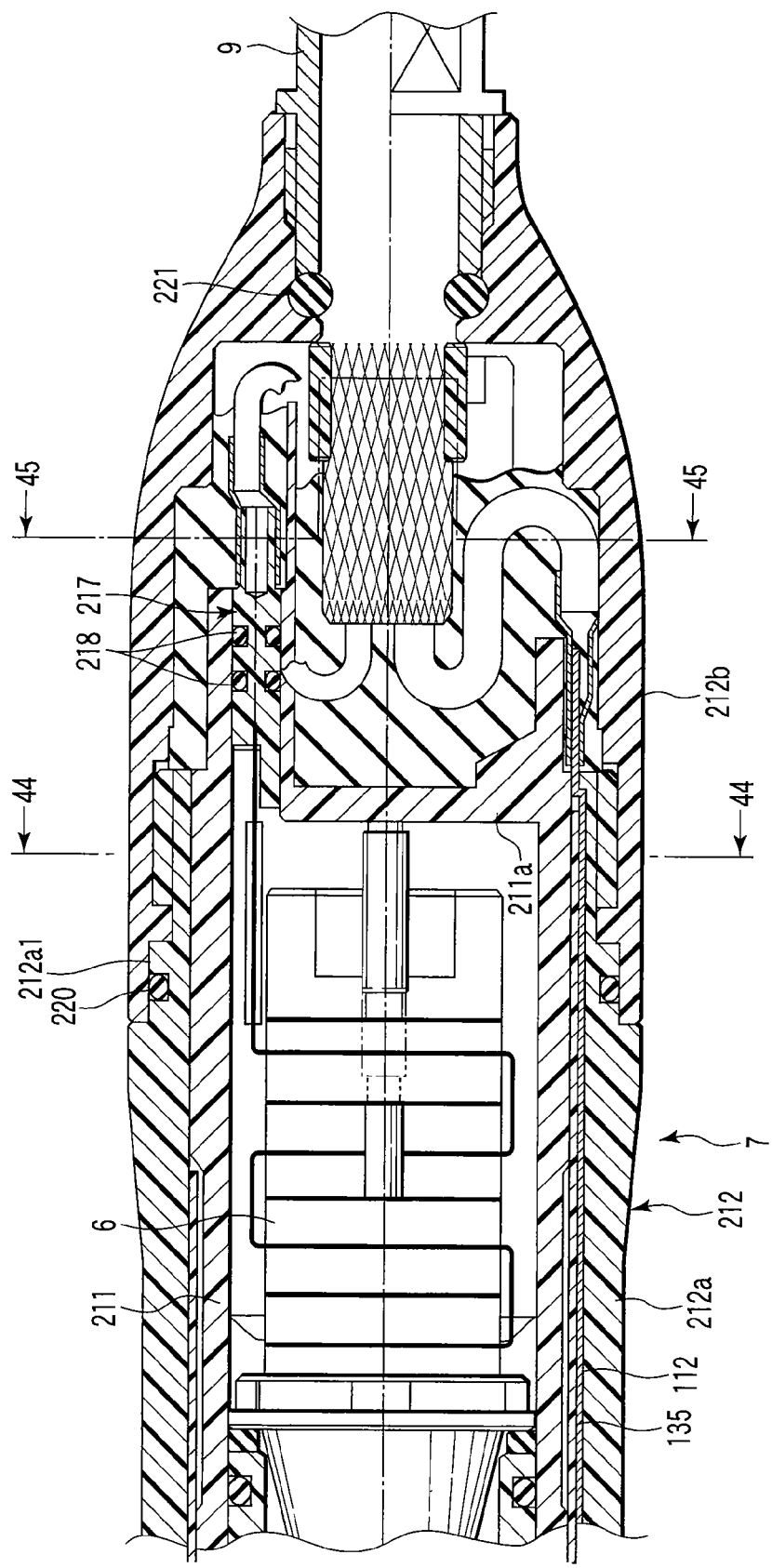
FIG. 42 is a longitudinal sectional view showing the rear end of the transducer unit.

FIG. 41 shows an internal configuration of the front end of the transducer unit 2, and FIG. 42 shows an internal configuration of the rear end of the transducer unit 2. The transducer cover 7 mainly has a cylindrical storage portion 211, and a tubular casing portion 212. The storage portion 211 is formed of a resin material which is an insulator, and stores the ultrasonic transducer 6. The casing portion 212 is formed of a resin material which is an insulator, and installed outside the storage portion 211.

As shown in FIG. 41, a ring-shaped transducer attaching member 213 is fixed to the inner peripheral surface at the distal end of the storage portion 211. In the ultrasonic transducer 6, a transducer flange 6a whose diameter is larger than those of the other parts is disposed at the end coupling to the proximal end of the horn 10 on the side of the probe unit 3. This transducer flange 6a is fixed in collision with the transducer attaching member 213 of the storage portion 211. A seal ring 214 is disposed between the transducer attaching member 213 and the transducer flange 6a. On the inner peripheral surface at the distal end of the transducer attaching member 213, a first O-ring 215 is attached to a surface contacting the ultrasonic transducer 6. On the outer peripheral surface at the proximal end of the transducer attaching member 213, a second O-ring 216 is attached to a surface contacting the inner peripheral surface of the storage portion 211.

As shown in FIG. 42, a shut-off wall 211a for blocking the side of the proximal end of the storage portion 211 is formed on the side of the proximal end of the storage portion 211. In parts of this shut-off wall 211a, there are formed three wiring line connecting portions 217 for connecting to some of the wiring lines within the cable 9, that is, the two wiring lines 101 and 102 for the ultrasonic transducer and the wiring line 103 for the high-frequency conduction (see FIG. 48). The wiring line connecting portions 217 are sealed with seal members 218, as shown in FIG. 42.

The casing portion 212 has a front casing 212a shown in FIG. 41, and a rear casing 212b shown in FIG. 42. A connection cylindrical portion 121 is formed at the distal end of the front casing 212a. A leaf-spring-shaped C ring 122 in which a part of a ring is cut off is attached onto the outer peripheral surface of the connection cylindrical portion 121. Inside the connection cylindrical portion 121, there is formed a stepped contact receiving portion 126 which is formed so that its outside diameter decreases stepwise toward a distal end side thereof. This contact receiving portion 126 has three steps of (first to third) cylindrical portions 123 to 125 which are provided to protrude forward from the distal end of the connection cylindrical portion 121 and which have differently dimensioned outside diameters.

The first cylindrical portion 123 has the smallest outside diameter, and the largest length of protrusion from the distal end of the connection cylindrical portion 121. The second cylindrical portion 124 has an outside diameter larger than that of the first cylindrical portion 123, and the length of its protrusion from the distal end of the connection cylindrical portion 121 is smaller than that of the first cylindrical portion 123. The third cylindrical portion 125 has the largest outside diameter, and the length of its protrusion from the distal end of the connection cylindrical portion 121 is smaller than that of the second cylindrical portion 124.

Figure 46:
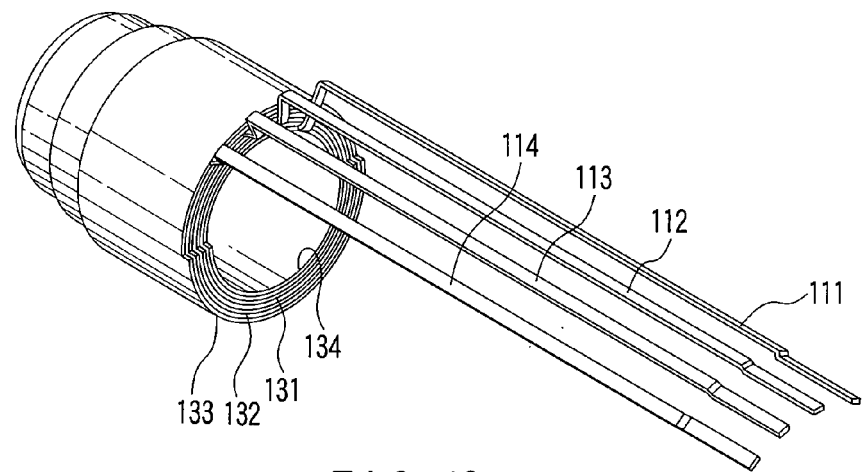
FIG. 46 is a perspective view showing how contact members and conducting plates of the transducer unit of the ultrasonic operating apparatus in the first embodiment are disposed.
Figure 47:
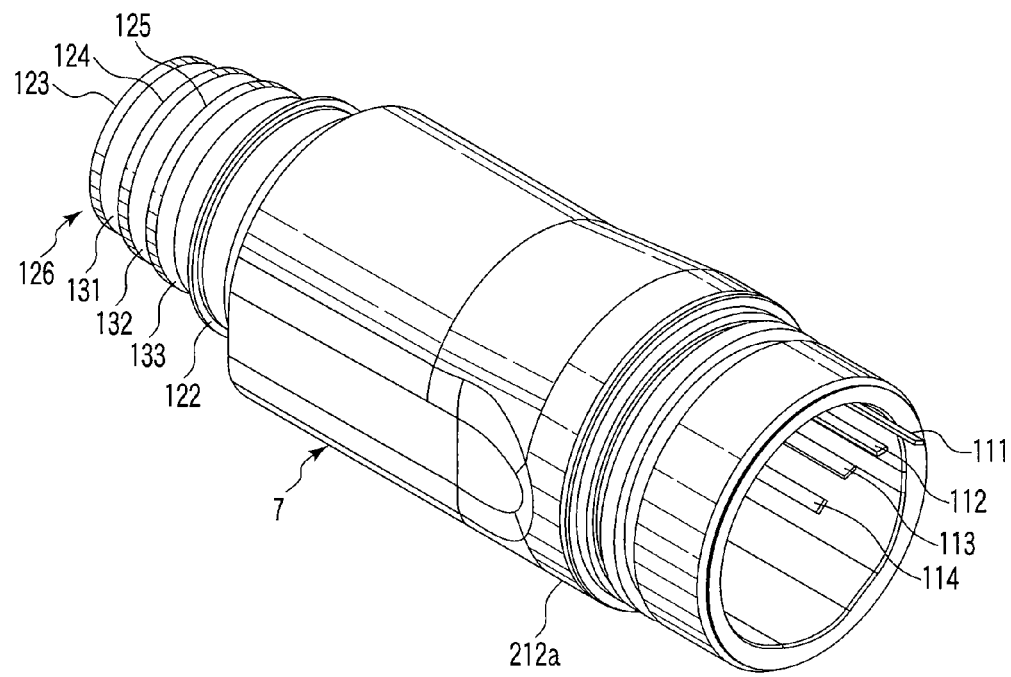
FIG. 47 is a perspective view showing a casing of the transducer unit of the ultrasonic operating apparatus in the first embodiment.

A cylindrical first contact member 131 is attached onto the outer peripheral surface of the first cylindrical portion 123. In the same manner, a cylindrical second contact member 132 is attached onto the outer peripheral surface of the second cylindrical portion 124, and a cylindrical third contact member 133 is attached onto the outer peripheral surface of the third cylindrical portion 125. As shown in FIG. 46, a second conducting plate (electric path element) 112 in the form of a flat plate for electric connection is connected to the first contact member 131, a third conducting plate (electric path element) 113 in the form of a flat plate is connected to the second contact member 132, and a fourth conducting plate (electric path element) 114 in the form of a flat plate is connected to the third contact member 133. A cylindrical fourth contact member 134 is attached onto the inner peripheral surface of the first cylindrical portion 123. The fourth contact member 134 is connected to a first conducting plate (electric path element) 111.

Figure 43:
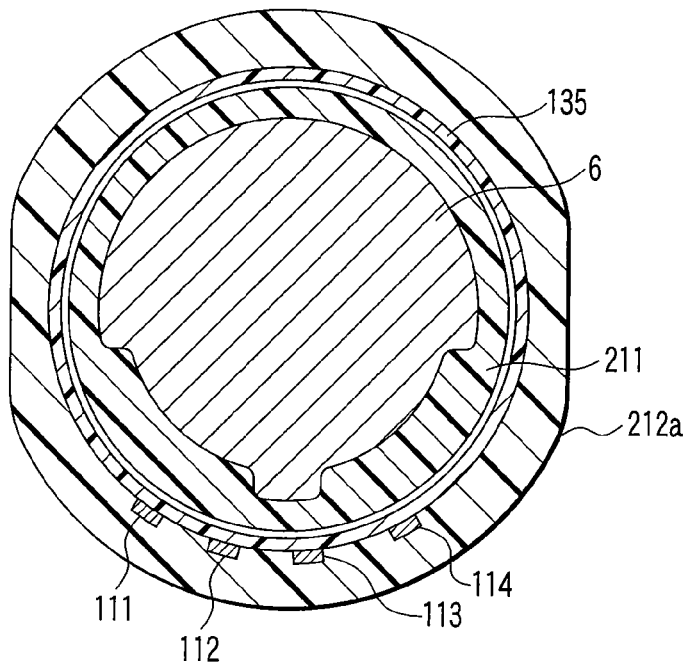
FIG. 43 is a sectional view along the 43-43 line in FIG. 41.
Figure 44:
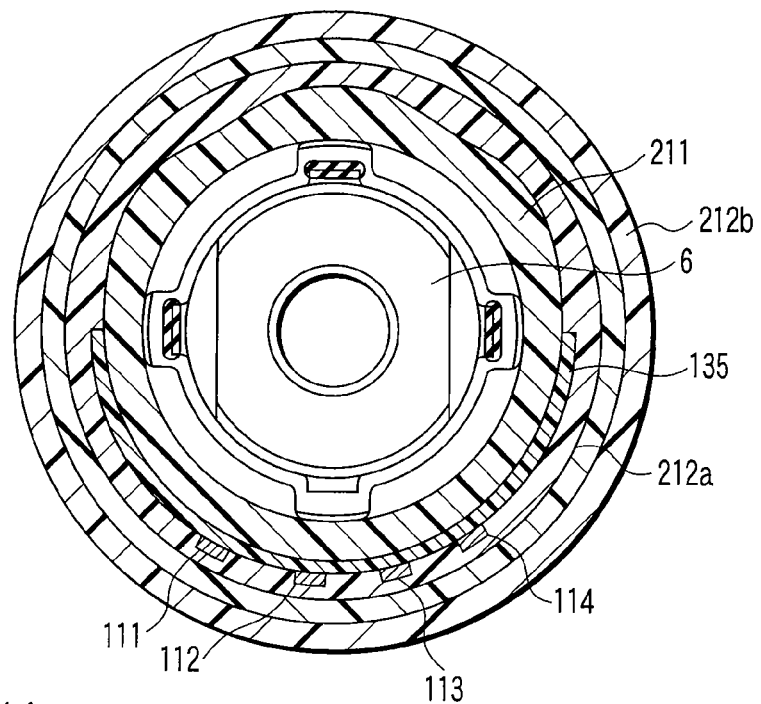
FIG. 44 is a sectional view along the 44-44 line in FIG. 42.

The first conducting plate 111, the second conducting plate 112, the third conducting plate 113 and the fourth conducting plate 114 linearly extend in parallel with the central line of the casing portion 212 toward the proximal end of the storage portion 211. As shown in FIGS. 43 and 44, these four conducting plates 111 to 114 are provided side by side on parts diametrically equal with respect to the central line of the ultrasonic transducer 6 along a circumferential direction thereof. Further, these four conducting plates 111 to 114 are integrally molded together with the front casing 212a to be buried in the inner peripheral surface of the front casing 212a. Thus, these four conducting plates 111 to 114 are disposed between the front casing 212a and the storage portion 211.

A cylindrical member 135 made of a resin is disposed on the outer peripheral surface at the distal end of the storage portion 211. The distal end of the cylindrical member 135 is bent along the inner peripheral surface of the contact receiving portion 126, and provided to extend onto the side of the inner peripheral surface of the fourth contact member 134. On the outer peripheral surface at the distal end of the storage portion 211, a third O-ring 219 is attached to a surface contacting the cylindrical member 135.

A ring-shaped small-diameter portion 212a1 is formed on the outer peripheral surface at the proximal end of the front casing 212a. The distal end of the rear casing 212b is coupled to this small-diameter portion 212a1 in an externally fitted state. On the outer peripheral surface of the small-diameter portion 212a1 of the front casing 212a, a fourth O-ring 220 is attached to a surface contacting the rear casing 212b.

The proximal ends of the first to fourth conducting plates 111 to 114 are provided to extend on the outer peripheral surface at the proximal end of the storage portion 211. The distal end of the other wiring line 104 for high-frequency conduction is connected to the first conducting plate 111. The three wiring lines 105, 106 and 107 are connected to the second to fourth conducting plates 112 to 114, respectively.

On the inner peripheral surface at the proximal end of the rear casing 212b, a fifth O-ring 221 is attached to a surface contacting the cable 9. Thus, the joint between the rear casing 212b and the cable 9 is sealed with the fifth O-ring 221.

When the handle unit 4 is coupled to the transducer unit 2, the contact unit 66 of the handle unit 4 is connected to the front end of the transducer unit 2. At this point, the electrode member 87A of the contact unit 66 is connected to the first contact member 131 of the transducer unit 2. At the same time, the electrode member 87B of the contact unit 66 is connected to the second contact member 132 of the transducer unit 2, the electrode member 87C of the contact unit 66 is connected to the third contact member 133 of the transducer unit 2, and the C-shaped electric contact member 96 of the contact unit 66 is connected to the fourth contact member 134 of the transducer unit 2.

Next, effects of the present embodiment will be described. In the hand piece 1 of the ultrasonic operating apparatus of the present embodiment, the four units including the transducer unit 2, the probe unit 3, the handle unit 4 and the sheath unit 5 are detachable, as shown in FIG. 2. During the use of the hand piece 1, the transducer unit 2 is coupled to the probe unit 3. Thus, the first high-frequency electric path 13 for transmitting the high-frequency current is formed in the combination of the transducer unit 2 and the probe unit 3.

Subsequently, the handle unit 4 is coupled to the sheath unit 5. When the handle unit 4 is coupled to the sheath unit 5, the connecting pipe member 34 is inserted into the rotation transmitting member 71 of the handle unit 4 while the pinch member 32 of the sheath unit 5 is being gripped. When the sheath unit 5 is coupled to the handle unit 4, the engaging lever 43 on the side of the handle unit 4 is held while being stranded on the inclined surface of the guide groove 41 of the pinch member 32 of the sheath unit 5, as shown in FIGS. 31 and 32. At this point, as shown in FIG. 17A, the engaging lever 43 is held at the position where the shape of the inner peripheral surface of the conductive rubber ring 94b corresponds to the engaging portion 46 of the outer peripheral flange portion 33b, that is, in a situation where the three corner portions 46b of the outer peripheral flange portion 33b correspond to the three corner portions 94b2 of the conductive rubber ring 94b. Therefore, the outer peripheral flange portion 33b of the sheath unit 5 is inserted straight into the conductive rubber ring 94b. During this insertion operation, the conductive rubber ring 94b is held at the non-compression position where it is in the natural state, as shown in FIG. 17A. In this state, there is no conduction between the sheath unit side electric path 40 and the handle unit side electric path 95.

Then, after this insertion operation is finished, the pinch member 32 of the sheath unit 5 is rotated in the direction around the axis with respect to the handle unit 4. Owing to this operation, the engaging lever 43 on the side of the handle unit 4 engages in an inserted state with the engaging concave portion 42 at one end of the guide groove 41, as shown in FIGS. 33 and 34. At this point, the conductive rubber ring 94b is switched to the pressure-contact position at which the conductive rubber ring 94b is placed in pressure-contact with the three corner portions 46b of the outer peripheral flange portion 33b, as shown in FIG. 17B. This permits conduction, via the conductive rubber ring 94b, between the sheath unit side electric path 40 and the handle unit side electric path 95. As a result, the second high-frequency electric path 97 for transmitting a high-frequency current is formed in the combination of the sheath unit 5 and the handle unit 4.

During this rotational operation of the sheath unit 5 in a direction around the axis, the pair of engaging pins 45 on the side of the handle unit 4 removably engages with the engaging grooves 44a at the terminal ends of the guide grooves 44 of the sheath unit 5 at the same time. Thus, the spring bearing member 64 on the side of the handle unit 4 is coupled to the connecting pipe member 34 on the side of the sheath unit 5 via the engaging pins 45. As a result, the operation force on the side of the handle unit 4 during the operation of closing the movable handle 49 with respect to the fixed handle 47 can be transmitted to the drive shaft 21 of the jaw 17 on the side of the sheath unit 5. This is the state where the sheath unit 5 is coupled to the handle unit 4.

Subsequently, the combination of the sheath unit 5 and the handle unit 4 and the combination of the ultrasonic transducer 6 and the probe unit 3 are set to be united into one. During this setting operation, the contact unit 66 of the handle unit 4 is connected to the front end of the transducer unit 2. At this point, the electrode member 87A of the contact unit 66 is connected to the first contact member 131 of the transducer unit 2. At the same time, the electrode member 87B of the contact unit 66 is connected to the second contact member 132 of the transducer unit 2, the electrode member 87C of the contact unit 66 is connected to the third contact member 133 of the transducer unit 2, and the C-shaped electric contact member 96 of the contact unit 66 is connected to the fourth contact member 134 of the transducer unit 2. Thus, the second high-frequency electric path 97 of the combination of the sheath unit 5 and the handle unit 4 is connected to the wiring line 104 for the high-frequency conduction within the cable 9. Further, the three wiring lines 105, 106 and 107 within the cable 9 are connected to the wiring line circuit board 92 within the switch holding portion 51. This is the state where the setting of the hand piece 1 is finished.

Then, during the use of this hand piece 1, the movable handle 49 is closed with respect to the fixed handle 47, such that the drive shaft 21 is axially moved in conjunction with the operation of this movable handle 49, and the jaw 17 is driven to open/close with respect to the probe distal end 3a of the probe unit 3 in conjunction with the axial back-and-forth movement of the drive shaft 21. Thus, the living tissue is gripped between the jaw 17 and the probe distal end 3a of the probe unit 3.

In this state, one of the coagulation switch button 54 and the incision switch button 55 of the fixed handle 47 is selectively pushed. When the coagulation switch button 54 is pushed, electricity is conducted in the first high-frequency electric path 13 for conducting a high-frequency current to the probe distal end 3a of the probe unit 3 and in the second high-frequency electric path 97 for conducting a high-frequency current to the jaw main body 28 of the sheath unit 5. Thus, two bipolar electrodes for the high-frequency treatment are formed by the probe distal end 3a of the probe unit 3 and the jaw main body 28 of the sheath unit 5. Then, the high-frequency current is conducted across the two bipolar electrodes formed by the probe distal end 3a of the probe unit 3 and the jaw main body 28 of the sheath unit 5, such that the living tissue between the jaw 17 and the probe distal end 3a of the probe unit 3 can be subjected to the high-frequency treatment by the bipolar.

When the incision switch button 55 is pushed, a drive current is conducted to the ultrasonic transducer 6 simultaneously with the high frequency conduction, and the ultrasonic transducer 6 is driven. Thus, the ultrasonic vibrations from the ultrasonic transducer 6 are transmitted to the probe distal end 3a via the vibration transmitting member 11, such that the treatment such as the incision or removal of the living tissue can be administered using the ultrasonic waves simultaneously with the high frequency conduction. In addition, the ultrasonic waves can also be used to coagulate the living tissue.

Furthermore, during the rotational operation of the swing operation knob 50, the rotational operation of the rotation transmitting member 71 which rotates together with the swing operation knob 50 is transmitted to the side of the spring bearing member 64 via the pins 81. Thus, during the rotational operation of the swing operation knob 50, the set unit of the rotation transmitting member 71, the pins 81, the spring bearing member 64, the slider member 65 and the coil spring 67 within the holding cylinder 48 is driven to integrally rotate in a direction around the axis together with the swing operation knob 50. Moreover, the rotational operation force of the swing operation knob 50 is transmitted to the vibration transmitting member 11 of the probe unit 3 via the tubular member 98 which rotates together with the spring bearing member 64 within the holding cylinder 48. Thus, the set unit within the holding cylinder 48 and the combination of the transducer unit 2 and the probe unit 3 are driven to integrally rotate together in a direction around the axis.

Therefore, the configuration described above provides the following advantages: according to the present embodiment, the four conducting plates 111 to 114 are provided between the storage portion 211 and the casing portion 212 of the transducer cover 7, such that the structure of the wiring lines inside the storage portion 211 can be simplified to save space. Therefore, the performance of sealing the ultrasonic transducer 6 inside the storage portion 211 can be enhanced, and the vapor density in the transducer unit 2 can be increased, such that it is possible to carry out the task of sterilizing the transducer unit 2 under a high-temperature and high-pressure environment.

Furthermore, the first conducting plate 111, the second conducting plate 112, the third conducting plate 113 and the fourth conducting plate 114 which are a plurality of electric paths for electric connection are provided side by side on the diametrically equal parts (on the same circumference) with respect to the central line of the ultrasonic transducer 6 along the circumferential direction thereof, such that the diameter of the casing portion 212 can be reduced even if a plurality of electric paths are disposed in the casing portion 212.

Moreover, the integral molding of the four conducting plates 111 to 114 with the front casing 212a of the casing portion 212 can facilitate the assembly of the transducer unit 2. The conducting plates 111 to 114 may be flexible substrates or wiring lines provided by vapor deposition.

Furthermore, in the present embodiment, the stepped contact receiving portion 126 is formed at the distal end of the front casing 212a, the first contact member 131 is attached onto the outer peripheral surface of the first cylindrical portion 123, the second contact member 132 is attached onto the outer peripheral surface of the second cylindrical portion 124, the third contact member 133 is attached onto the outer peripheral surface of the third cylindrical portion 125, and the fourth contact member 134 is attached onto the inner peripheral surface of the first cylindrical portion 123. Thus, electric contacts can be provided inside and outside the contact receiving portion 126, so that it is possible to decrease the diameter of a complicated electric contact portion having multiple contacts of the transducer unit 2.

Still further, in the configuration of the hand piece 1 of the ultrasonic operating apparatus of the present embodiment, there are incorporated, in one cable 9 at the rear end of the transducer unit 2, the two wiring lines 101 and 102 for the ultrasonic transducer, the two wiring lines 103 and 104 for high-frequency conduction, and the three wiring lines 105, 106 and 107 connected to the wiring line circuit board 92 within the switch holding portion 51, as shown in FIG. 48. It is therefore not necessary to connect a plurality of cables to the hand piece 1, so that the operability of the hand piece 1 can be enhanced.

Further yet, in the present embodiment, the switch holding portion 51 is provided in the fixed handle 47, and the coagulation switch button 54 and the incision switch button 55 are incorporated in the fixed handle 47. The connection wiring lines of the coagulation switch button 54 and the incision switch button 55 are disposed within the hand piece 1, and connected to the three wiring lines 105, 106 and 107 incorporated in one cable 9 at the rear end of the transducer unit 2. Therefore, the connection wiring lines for the coagulation switch button 54 and the incision switch button 55 are not coupled to the hand piece 1, for example, as in the case where the coagulation switch button 54 and the incision switch button 55 are externally attached to the hand piece 1. As a result, the number of connecting cords connected to the hand piece 1 can be further reduced. In addition, it is possible to facilitate the provision of the electric path from the cable 9 to the electric contact.

Moreover, FIGS. 49 and 50 show a second embodiment of the ultrasonic operating apparatus of the present invention. In the configuration of the present embodiment, the function of a hand switch of the fixed handle 47 is automatically switched depending on the kind of the hand piece 1 connected to the power supply main unit 8 of the ultrasonic operating apparatus. It is to be noted that the same signs are assigned to the same parts in FIGS. 49 and 50 as those in the first embodiment, and those parts will not be described.

That is, in the present embodiment, FIG. 49 show there are connected, to the power supply main unit 8, a first hand piece 401 (corresponding to the hand piece 1 in the first embodiment) capable of the bipolar high-frequency treatment and ultrasonic treatment, and a second hand piece 402 exclusive to the ultrasonic treatment.

The power supply main unit 8 has an ultrasonic wave output section 411, a high-frequency output section 412, a judging section 413 and a control section 414. The ultrasonic wave output section 411, the high-frequency output section 412 and the judging section 413 are connected to the control section 414.

FIG. 50 shows internal electric wiring lines of a connector portion 415 provided in the cable 9 of the hand piece 401, 402. Inside the connector portion 415, there is provided a model setting resistor 416 set to a different resistance value for each of the hand pieces 401 and 402.

When the connector portion 415 of the cable 9 of the hand piece 401, 402 is connected to the power supply main unit 8, the resistance value of the resistor 416 is detected by the judging section 413 of the power supply main unit 8. Then, the model of the hand piece 401, 402 connected to the power supply main unit 8 is judged in accordance with the detected resistance.

Data on the model of the hand piece 401, 402 judged by the judging section 413 is output to the control section 414. This control section 414 automatically switches the function of the hand switch of the fixed handle 47 depending on the model of the hand piece 401, 402. That is, when the first hand piece 401 is connected to the power supply main unit 8, the coagulation switch 54a functions as an on/off switch for the bipolar high-frequency treatment, and the incision switch 55a functions as an on/off switch for a combination of the ultrasonic treatment and the bipolar high-frequency treatment.

On the other hand, when the second hand piece 402 is connected to the power supply main unit 8, the coagulation switch 54a functions as an on/off switch for driving the ultrasonic transducer 6 under a condition where its output is set, and the incision switch 55a functions as an on/off switch for driving the ultrasonic transducer 6 under a condition where its output is high.

Therefore, the configuration described above provides the following advantages: in the present embodiment, the function of the hand switch of the fixed handle 47 can be automatically switched depending on the kind of the hand piece 1 connected to the power supply main unit 8 of the ultrasonic operating apparatus. There is thus no need for troublesome tasks of, for example, changing the setting of the power supply main unit 8 depending on the model of the hand piece 401, 402 connected to the power supply main unit 8 of the ultrasonic operating apparatus, and workability can be enhanced.

It is to be noted that the present invention is not limited to the embodiments described above, and various modifications can be made without departing from the spirit of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical instrument comprising an ultrasonic apparatus for surgically operating on a patient, the ultrasonic apparatus comprising:
   an ultrasonic transducer which generates ultrasonic vibrations;
   a probe portion for surgically treating the patient and which has a distal end and a proximal end, the proximal end being coupled to the ultrasonic transducer, the ultrasonic vibrations generated from the ultrasonic transducer being transmitted to the probe portion;
   a storage portion which stores the ultrasonic transducer in an internal space thereof;
   a cylindrical casing portion which has a distal end and a proximal end, covers the storage portion and is in close contact with the storage portion in a thickness direction, the thickness direction extending in a direction perpendicular to a longitudinal direction of the storage portion and the cylindrical casing portion;
   a first electric path and a second electric path provided to extend between an electric contact disposed at the distal end of the cylindrical casing portion and an electric cable connecting portion provided at the proximal end of the casing portion; and
   an electric cable which has a distal end and a proximal end, the electrical cable proximal end being connected to a power supply unit, the electric cable distal end being coupled to the electric cable connecting portion,
   the first electric path and the second electric path being sandwiched between the storage portion and the cylindrical casing portion in the thickness direction,
   the electric contact having:
   a contact receiving portion which is formed so that an outside diameter of the cylindrical casing portion decreases stepwise toward the distal end thereof;
   an outer side contact installed in the contact receiving portion, disposed on an outer peripheral surface of the distal end of the cylindrical casing portion and connected to the first electric path; and
   an inner side contact disposed on an inner peripheral surface of the distal end of the cylindrical casing portion and connected to the second electric path, said first electric path and said second electric path and said outer and inner side contacts being positioned and configured to provide at least one of control and surgical operating energy for said surgical instrument.

2. The surgical instrument comprising the ultrasonic operating apparatus according to claim 1, wherein
   the first electric path and the second electric path have a plurality of electric path elements, and
   the plurality of electric path elements are provided side by side on diametrically equal parts of an outer peripheral surface of the transducer along a circumferential direction thereof.

3. The surgical instrument comprising the ultrasonic operating apparatus according to claim 2, wherein
   the plurality of electric path elements include at least one of electric path elements of a current for a hand switch and electric path elements of a current for a high-frequency treatment.

4. The surgical instrument comprising the ultrasonic operating apparatus according to claim 2, wherein the plurality of electric path elements are disposed in a direction different from a diametrical direction of the cylindrical casing portion.

5. The surgical instrument comprising the ultrasonic operating apparatus according to claim 2, wherein
the plurality of electric path elements are integrally molded to be buried in the cylindrical casing portion.

6. An ultrasonic operating apparatus comprising:
an ultrasonic transducer which generates ultrasonic vibrations;
a probe portion which has a distal end and a proximal end, the proximal end being coupled to the ultrasonic transducer, the ultrasonic vibrations generated output from the ultrasonic transducer being transmitted to the probe portion;
a first high-frequency electric path which is provided in a combination of the ultrasonic transducer and the probe portion and which transmits a high-frequency current;
a sheath portion which is formed by a cylindrical member having a distal end and a proximal end and into which the probe portion is removably inserted, the sheath portion having a jaw swingably supported on the distal end thereof to be opposite to the probe portion;
a handle portion which is detachably coupled to the proximal end of the sheath portion and which opens and closes the jaw with respect to the probe portion, the handle portion having a transducer connecting portion to which the ultrasonic transducer is detachably connected, and a hand switch which selects a function of the probe portion;
a second high-frequency electric path which is provided in a combination of the sheath portion and the handle portion and which transmits a high-frequency current;
a storage portion which stores the ultrasonic transducer in an internal space thereof;
a cylindrical casing portion which has a distal end and a proximal end and which is installed outside the storage portion and is in close contact with the storage portion in a thickness direction, the thickness direction extending, in a direction perpendicular to a longitudinal direction of the storage portion and the cylindrical casing portion;
an electric cable which has a distal end and a proximal end, the proximal end being connected to a power supply unit, the distal end being coupled to an electric cable connecting portion, the electric cable having at least an electric wiring line for the ultrasonic transducer, a high-frequency conducting electric wiring line connected to the first and second high-frequency electric paths, and a hand switch electric wiring line connected to the hand switch;
the electric cable connecting portion disposed at the proximal end of the cylindrical casing portion, the electric cable connecting portion having at least a transducer electric connecting portion connected to the electric wiring line for the ultrasonic transducer, two high-frequency conducting electric connecting portions respectively connected to the high-frequency conducting electric wiring lines, and a hand switch electric connecting portion connected to the hand switch electric wiring line; and
an electric contact disposed at the distal end of the cylindrical casing portion, the electric contact having:
a contact receiving portion which is formed so that an outside diameter of the cylindrical casing portion decreases stepwise toward the distal end side thereof;
an outer side contact installed in the contact receiving portion, disposed on an outer peripheral surface of the distal end of the cylindrical casing portion and connected to the first high-frequency electric path; and
an inner side contact disposed on an inner peripheral surface of the distal end of the cylindrical casing portion and connected to the second high-frequency electric path,
the first high-frequency electric path and the second high-frequency electric path being disposed between the storage portion and the cylindrical casing portion.

* * * * *